United States Patent
Leffler et al.

(10) Patent No.: US 8,703,720 B2
(45) Date of Patent: Apr. 22, 2014

(54) GALACTOSIDE INHIBITORS OF GALECTINS

(75) Inventors: Hakon Leffler, Lund (SE); Ulf J. Nilsson, Lund (SE); Henrik Von Wachenfeldt, Gothenburg (SE)

(73) Assignee: Galecto Biotech AB, Lund (SE)

( * ) Notice: Subject to any disclaimer, the term of this patent is extended or adjusted under 35 U.S.C. 154(b) by 0 days.

(21) Appl. No.: 13/266,960

(22) PCT Filed: Apr. 26, 2010

(86) PCT No.: PCT/SE2010/050458
§ 371 (c)(1),
(2), (4) Date: Mar. 7, 2012

(87) PCT Pub. No.: WO2010/126435
PCT Pub. Date: Nov. 4, 2010

(65) Prior Publication Data
US 2012/0165277 A1    Jun. 28, 2012

Related U.S. Application Data

(60) Provisional application No. 61/173,284, filed on Apr. 28, 2009.

(51) Int. Cl.
C07H 19/12 (2006.01)
C07H 5/10 (2006.01)
A61K 31/7056 (2006.01)
A61K 31/7034 (2006.01)

(52) U.S. Cl.
USPC ............ 514/24; 536/17.4; 536/17.9; 536/54; 514/23; 514/35

(58) Field of Classification Search
None
See application file for complete search history.

(56) References Cited

FOREIGN PATENT DOCUMENTS

| WO | 02057284 A1 | 7/2002 |
| WO | 03026494 A2 | 4/2003 |
| WO | 2005113568 A1 | 12/2005 |
| WO | 2005113569 A1 | 12/2005 |

OTHER PUBLICATIONS

Zips, Daniel et al., In Vivo, "New Anticancer Agents: In Vitro and In Vivo Evaluation", 2005, vol. 19, pp. 1-8.*
Perone et al. "Suppression of Autoimmune Diabetes by Soluble Galectin-1", J. Immunol. 2009, vol. 182, p. 2641-2653.
Pienta et al. "Inhibition of Spontaneous Metastasis in a Rat Prostate Cancer Model by Oral Administration of Modified Citrus Pectin", Journal of the National Cancer Institute Mar. 1, 1995, vol. 87, No. 5, p. 348-353.
Salameh et al. "3-(1,2,3-Triazol-1-yl)-1-thio-galactosides as small, efficient, and hydrolytically stable inhibitors of galectin-3", Bioorganic & Medicinal Chemistry Letters 2005, vol. 15, p. 3344-3346.
Seetharaman et al. "X-ray Crystal Structure of the Human Galectin-3 Carbohydrate Recognition Domain at 2.1-A Resolution", The Journal of Biological Chemistry, Issue of May 22, 1998, vol. 273, No. 21, p. 13047-13052.
Sorme et al. "Low Micromolar Inhibitors of Galectin-3 Based on 3'-Derivatization of N-Acetyllactosamine", Chem. Bio. Chem. 2002, vol. 3, p. 183-189.
Sorme et al. "Flurescence Polarization to Study Galectin-Ligand Interactions", Methods in Enzymology 2003, vol. 362, p. 504-512.
Sorme et al. "Design and Synthesis of Galectin Inhibitors", Methods in Enzymology 2003, vol. 363, p. 157-157-169.
Toscano et al. "Differential glycosylation of TH1, TH2 and TH-17 effector cells selectively regulates susceptibility to cell death", Nature Immunology Aug. 2007,vol. 8, No. 8, p. 825-834.
Watt et al. "The involvement of galectin-1 in skeletal muscle determination, differentiation and regeneration", Glycoconjugate Journal 2004, vol. 19, p. 615-619.
Massa et al. "L-29, an Endogenous Lectin, Binds to Glycoconjugate Ligands with Positive Cooperativity", Biochemistry 1993, vol. 32, p. 260-267.
MacKinnon et al. "Regulation of Alternative Macrophage Activation by Galectin-3", The Journal of Immunology 2008, vol. 180, p. 2650-2658.
Barondes et al. "Galectins: Structure and Function of a Large Family of Animal Lectins", The Journal of Biological Chemistry 1994, vol. 269, No. 33, Issue of Aug. 19, p. 20807-20810.
Garner et al. Galectin-glycan lattices regulate cell-surface glycoprotein organization and signalling, Biochem. Soc. Trans. Dec. 2008, vol. 36, Pt.6, p. 1472-1477.
Gendronneau et al. "Galectin-7 in the Control of Epidermal Homeostasis after Injury", Molecular Biology of the Cell Dec. 2008, vol. 19, p. 5541-5549.
Thijssen et al. "Galectins in the tumor endothelium: opportunities for combined cancer therapy", Blood 2007, vol. 110, p. 2819-2827.
Sato et al. "Seeing strangers or announcing "danger": Galectin-3 in two models of innate immunity", Glycoconjugate Journal 2004, vol. 19, p. 583-591.

(Continued)

Primary Examiner — Layla Bland
Assistant Examiner — Bahar Craigo
(74) Attorney, Agent, or Firm — Brooks Kushman P.C.

(57) ABSTRACT

Compounds having an effect as i.a. galectin inhibitors, to the use of said compounds as a medicament, as well as for the manufacture of a medicament for treatment of disorders relating to the binding of galectin to receptors in a mammal, where in the galectin is preferably a galectin-3. The novel compounds are defined by the general formula:

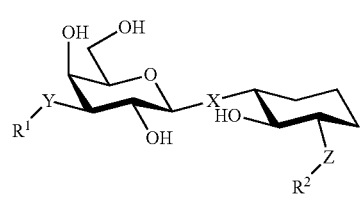

(I)

19 Claims, 3 Drawing Sheets

(56) References Cited

OTHER PUBLICATIONS

Karlsson et al. "Galectin-3 Activates the NADPH-Oxidase in Exudated but not Peripheral Blood Neutrophils", Blood 1998, vol. 91, p. 3430-3438.
Almkvist et al. "Lipopolysaccharide-Induced Gelatinase Granule Mobilization Primes Neutrophils for Activation by Galectin-3 and Formylmethionyl-Leu-Phe", Infection and Immunity 2001, vol. 69, p. 832-837.
Arnusch et al. "Interference of the galactose-dependent binding of lectins by novel pentapetide ligands", Bioorganic & Medicinal Chemistry Letters 2004, vol. 14, p. 1437-1440.
Ogawa et al. "The speciation of conger eel galectins by rapid adaptive evolution", Glycoconjugate Journal 2004, vol. 19, p. 451-458.
Juflejt et al. "Galectin-4 in normal tissues and cancer", Glycoconjugate Journal 2004, vol. 20, p. 247-255.
Karima et al. "The molecular pathogenesis of endotoxic shock and organ failure", Molecular Medicine Today Mar. 1999, p. 123-132.
Leffler et al. "Galectins Structure and Function—A Synopsis", Results Probl. Cell Differ. 2001, vol. 33, p. 57-83.
Sacchettini et al. "Current Topics: Multivalent Protein-Carbohydrate Interactions. A New Paradigm for Supermolecular Assembly and Signal Transduction", Biochemistry Mar. 13, 2001, vol. 40, No. 10, p. 3009-3015.
Saegusa et al. "Galectin-3 Is Critical for the Development of the Allergic Inflammatory Response in a Mouse Model of Atopic Dermatitis", The American Journal of Pathology Mar. 2009, vol. 174, No. 3, p. 922-931.
Blois et al. "A pivotal role for galectin-1 in fetomaternal tolerance", Nature Medicine Dec. 2007, vol. 13, No. 12, p. 1450-1458.
Cumpstey et al. "C2-Symmetrical Thiodigalactoside Bis-Benzamido Derivatives as High-Affinity Inhibitors of Galectin-3: Efficient Lectin Inhibition through Double Arginine-Arene Interactions", Angew. Chem. Int. Ed. 2005, vol. 44, p. 5110-5112.
International Search Report for PCT/SE2010/050458, Completed by the Swedish Patent Office on Aug. 18, 2010, 4 Pages.
Ahmad et al. "Galectin-3 Precipitates as a Pentamer with Synthetic Multivalent Carbohydrates and Forms Heterogeneous Cross-linked Complexes", The Journal of Biological Chemistry 2004, vol. 279, Issue of Mar. 19, p. 10841-10847.
Andre et al. "Lactose-containing starburst dendrimers: influence of dendrimer generation and binding-site orientation of receptors (plant/animal lectins and immunoglobulins) on binding properties", Glycobiology 1999, vol. 9, No. 11, p. 1253-1261
Andre et al. "Persubstituted Cyclodextrin-based Glycoclusters as Inhibitors of Protein-Carbohydrate Recognition Using Purified Plant and Mammalian Lectins and Wild-Type and Lectin-Gene-Transfected Tumor Cells as Targets", Bioconjugate Chem 2004, vol. 15, p. 87-98.
Bresalier et al. "Metastatis of Human Colon Cancer is Altered by Modifying Expression of the B-Galactoside-Binding Protein Galectin 3", Gastroenterology 1998, vol. 115, p. 287-296.
Brewer. "Binding and cross-linking properties of galectins", Biochimica et Biophysics Acta 2002, vol. 1572, p. 255-262.
Cumpstey et al. "Double Affinity Amplification of Galectin-Ligand Interactions through Arginine-Arene Interactions: Synthetic, Thermodynamic, and Computational Studies with Aromatic Diamido Thiodigalactosides", Chem. Eur. J. 2008, vol. 14, p. 4233-4245.
David et al. "Design of a multivalent galactoside ligand for selective targeting of HPMA copolymer-doxorubicin conjugates to human colon cancer cells", European Journal of Cancer 2004, vol. 40, p. 148-157.
John et al. "Truncated Galectin-3 Inhibits Tumor Growth and Metastasis in Orthotopic Nude Mouse Model of Human Breast Cancer", Clin Cancer Res 2003, vol. 9, p. 2374-2383.
Leffler et al. "Introdection to galectins", Glycoconjugate Journal 2004, vol. 19, p. 433-440.
Yuri et al. "Galectin Structure", Trends in Glycoscience and Glycotechnology Jan. 1997, vol. 9, No. 45, p. 145-154.
Nangia-Makker et al. "Inhibition of Human Cancer Cell Growth and Metastasis in Nude Mice by Oral Intake of Modified Citrus Pectin", Journal of the National Cancer Institute Dec. 18, 2002, vol. 94, p. 1854-1862.
Platt et al. "Modulation of the Lung Colonization of B16-F1 Melanoma Cells by Citrus Pectin", Journal of the National Cancer Institute, vol. 84, No. 6, Mar. 18, 1992, p. 438-442.
Pohl et al. "Scope of Multivalent Ligand Function: Lactose-Bearing Neoglycopolymers by Ring-Opening Metathesis Polymerization", Synthesis 1999, No. SI, p. 1515-1519.
Poirier. "Roles of galectin in vivo", Biochem. Soc. Symp. vol. 69, p. 95-103.
Rubinstein et al. "Targeted inhibition of galectin-1 gene expression in tumor cells results in heightened T cell-mediated rejection: A potential mechanism of tumor-immune privilege", Cancer Cell Mar. 2004, vol. 5, p. 241-251.
Sano et al. "Human Galectin-3 Is a Novel Chemoattractant for Monocytes and Macrophages", J. Immunol. 2000, vol. 165, p. 2156-2164.
Sorme et al. "Fluorescence polarization as an analytical tool to evaluate galectin-ligand interactions", Analytical Biochemistry 2004, vol. 334, p. 36-47.
Sorme et al. "Structural and Thermodynamic Studies on Cation-II Interactions in Lectin-Ligand Complexes: High-Affinity Galectin-3 Inhibitors through Fine-Tuning of an Arginine-Arene Interaction", J. Am. Chem.Soc. 2005, vol. 127, p. 1737-1743.
Takenaka et al. "Galectin-3 and metastasis", Glycoconjugate Journal 2004, vol. 19, p. 543-549.
Trahey et al. "Cyclophilin C-associated protein: A normal secreted glycoprotein that down-modulates endotoxin and proinflammatory responses in vivo", PNAS USA Mar. 1999, vol. 96, p. 3006-3011.
Vrasidas et al. "Rigidified multivalent lactose molecules and their interactions with mammalian galectins: a route to selective inhibitors", OBC 2003, vol. 1, p. 803-810.
Patterson et al. "Understanding the biochemical activities of galectin-1 and galectin-3 in the nucleus", Glycoconjugate Journal 2004, vol. 19, p. 499-506.
Hsu et al. "Regulation of cellular homeostasis by galectins", Glycoconjugate Journal 2004, vol. 19, p. 507-515.
Ochieng et al. "Extracellular functions of galectin-3", Glycoconjugate Journal 2004, vol. 19, p. 527-535.
Bidon-Wagner et al. "Human galectin-8 isoforms and cancer", Glycoconjugate Journal 2004, vol. 19, p. 557-563.
Almkvist et al. "Galectins as inflammatory mediators", Glycoconjugate Journal 2004, vol. 19, p. 575-851.
Rabinovich et al. "Shedding light on the immunomodulatory properties of galectins: Novel regulators of innate and adaptive immune responses", Glycoconjugate Journal 2004, vol. 19, p. 565-573.
Pace et al. "Insect galectins:, Roles in immunity and development", Glyconjugate Journal 2004, vol. 19, p. 607-614.
Andre et al. "Identification of peptide ligands for malignancy-and growth-regulating galectins using random phage-display and designed combinatorial peptide libraries", Bioorganic & Medicinal Chemistry 2005, vol. 13, p. 563-573.
Chiariotti et al. "Galectin genes: Regulation of expression", Glycoconjugate Journal 2004, vol. 19, p. 441-449.
Rewer. "Thermodynmaic binding studies of galectin-1,-3,-7", Glycoconjugate Journal 2004, vol. 19, p. 459-465.
Scott et al. "Galectin-1: A bifunctional regulator of cellular proliferation", Glycoconjugate Journal 2004, vol. 19, p. 467-477.
Horie et al. "Galectin-1 plays essential roles in adult mammalian nervous tissues. Role of oxidized galectin-1", Glycoconjugate Journal 2004, vol. 19, p. 479-489.
Lipkowitz et al. "Galectin 9 is the sugar-regulated urate transporter/channel UAT", Glycoconjugate Journal 2004, vol. 19, p. 491-498.
Zick et al. "Role of galectin-8 as a modulator of cell adhesion and cell growth", Glycoconjugate Journal 2004, vol. 19, p. 517-526.
Grassadonia et al. "90K (Mac-2 BP) and galectins in tumor progression and metastasis", Glycoconjugate Journal 2004, vol. 19, p. 551-556.
Hirashima et al. "Galectin-9 in physiological and pathological conditions", Glycoconjugate Journal 2004, vol. 19, p. 593-600.

(56) References Cited

OTHER PUBLICATIONS

Young et al. "Galectins in parasite infection and allergic inflammation", Glycoconjugate 2004, vol. 19, p. 601-606.
Hughes. "Galectins in kidney development", Glycoconjugate Journal 2004, vol. 19, p. 621-629.
Dam et al. "Effects of Clustered Epitopes in Multivalent Ligand-Receptor Interactions", Current Topics Biochemistry 2008, vol. 47, p. 8470-8476.
Delacour et al. "Apical Sorting by Galectin-3-Dependent Glycoprotein Clustering", Traffic 2007, vol. 8, p. 379-388.
Delaine et al. "Galectin-Inhibitory Thiodigalactoside Ester Derivatives Have Antimigratory Effects in Cultured Lung and Prostate Cancer Cells", J. Med. Chem. 2008, vol. 51, p. 8109-8114.
Fortin et al. "Galectin-1 is Implicated in the Protein Kinase C ε/Vimentin-Controlled Trafficking of Integrin-β1 in Glioblastoma Cells", Brain Pathology 2008, p. 1-11.
Glinsky et al. "Inhibition of Human Breast Cancer Metastasis in Nude Mice by Synthetic Glycoamines", Cancer Research Advances in Brief Dec. 1, 1996, vol. 56, p. 5319-5324.
Houzelstein et al. "Phylogenetic Analysis of the Vertebrate Galectin Family", Molecular Biology and Evolution 2004, vol. 21, No. 7, p. 1177-1187.
Lau et al. "Complex N-Glycan Number and Degree of Branching Cooperate to Regulate Cell Proliferation and Differentiation", Cell Apr. 6, 2007, vol. 129, p. 123-134.
Lau et al. "Review: N-Glycans in Cancer Progression", Glycobiology 2008, vol. 18, No. 10, p. 750-760.
Leffler et al. "Specificity of Binding of Three Soluble Rat Lung Lectins to Substituted and Unsubstituted Mammalian β-Galactosides", The Journal of Biological Chemistry Issue of Aug. 5, 1986, vol. 261, No. 22, p. 10119-10126.
Brule et al. "Expression of galectins in cancer: A critical review", Glycoconjugate Journal 2004, vol. 19, p. 537-542.
Tejler et al. Bioorganic and Medicinal Chemistry Letters 2005, vol. 15, p. 2343-2345, "Synthesis of O-galactosylaldoximes as potent LacNAc-mimetic galectin-3 inhibitors."
Extended European Search Report for EP 10770027.0, Completed by the European Patent Office on Mar. 28, 2013, 7 Pages.

\* cited by examiner

GALACTOSIDE INHIBITORS OF GALECTINS

CROSS-REFERENCE TO RELATED APPLICATION

This application is the U.S. national phase of PCT Appln. No. PCT/SE2010/050458 filed Apr. 26, 2010 which claims benefit of U.S. provisional application 61/173,284 filed Apr. 28, 2009, the disclosures of which are incorporated in their entirety by reference herein.

TECHNICAL FIELD

The present invention relates to novel compounds, the use of said compounds as medicament and for the manufacture of a medicament for the treatment of any disorder relating to the binding of a galectin receptor in mammals. The invention also relates to pharmaceutical compositions comprising said novel compounds.

BACKGROUND ART

Galectins are proteins with a characteristic carbohydrate recognition domain (CRD) (Barondes et al., 1994; Leffler et al., 2004)(FIG. 1a). This is a tightly folded β-sandwich of about 130 amino acids (about 15 kDa) with the two defining features 1) a β-galactose binding site (C in FIGS. 1a and 2) sufficient similarity in a sequence motif of about seven amino acids, most of which (about six residues) make up the β-galactose binding site. However, adjacent sites (A,B,D,E in FIG. 1a) are required for tight binding of natural saccharides and different preferences of these give galectins different fine specificity for natural saccharides.

The recent completion of the human, mouse and rat genome sequences reveal about 15 galectins and galectin-like proteins in one mammalian genome with slight variation between species (Leffler et al., 2004; Houzelstein et al., 2004).

Galectin subunits can contain either one or two CRDs within a single peptide chain. The first category, mono-CRDs galectins, can occur as monomers or dimers (two types) in vertebrates. The by far best studied galectins are the dimeric galectin-1, and galectin-3 that is a monomer in solution but may aggregate and become multimeric upon encounter with ligands (Leffler et al., 2004; Ahmad et al., 2004). These were the first discovered galectins and are abundant in many tissues. However, our recent phylogenetic analysis (FIG. 2) suggest that galectins with two CRDs within a peptide chain, bi-CRD galectins, appear to be more ancient and more central to the family than previously thought and that most of mammalian mono-CRD galectins may have descended from one or the other CRD of a bi-CRD galectin.

There are now over 2500 publications on galectins in PubMed, with most, as mentioned above, about galectins-1 (>600) and -3 (>1100). Strong evidence suggests roles for galectins in e.g. inflammation and cancer, and development recently reviewed in a special issue (Leffler (editor), 2004b).

Galectins are synthesized as cytosolic proteins, without a signal peptide on free ribosomes. Their N-terminus is acetylated, a typical modification of cytosolic proteins, and they reside in the cytosol for a long time (not typical of secreted proteins). From there they can be targeted to the nucleus, specific cytososlic sites, or secreted (induced or constitutively) by a non-classical (non-ER-Golgi) pathway, as yet unknown, but possibly similar to the export of e.g. IL-1 (Leffler et al., 2004). They can also function in all these compartments; for galectin-3, solid evidence published in well respected journals support roles in RNA splicing in the nucleus, inhibition of apoptosis in the cytosol, and a variety of extracellular effects on cell signaling and adhesion (Patterson et al., Ochieng et al., Takenaka et al., Hsu et al. and others in Leffler (editor), 2004b). Galectin-7 and -12 also act in the cytosol by enhancing apoptosis and regulating the cell cycle and differentiation in certain cells (Hsu and Liu in Leffler (editor), 2004b). Most galectins act also extracellularly by cross-linking glycoproteins (e.g. laminin, integrins, and IgE receptors) possibly forming supramolecular ordered arrays (Brewer et al., 2002) and may thereby modulate cell adhesion and induce intracellular signals. Related to this, recent years have seen the emergence of a molecular mechanism of these galectin functions involving on formation of microdomains (lattices) within membranes, (Dam et al., 2008; Garner et al., 2008; Sacchettini et al., 2001) which in turn affects intracellular trafficking and cell surface presentation of glycoprotein receptors. (Delacour et al., 2007; Fortin et al., 2008; Lau et al., 2007; Lau et al. 2008) This has been documented in cell culture, in null mutant mice, (Blois et al., 2007; Gedronneau et al., 2008; Thijssen et al., 2007; Toscano et al., 2007; Saegusa et al., 2009) and animals treated with galectin (Blois et al., 2007; Perone et al., 2009) or galectin inhibitors. (John et al., 2003; Pienta et al., 1995; Glinsky et al., 1996)

The present invention relates mainly to galectin-1 inhibitors and galectin-3 inhibitors, but its principles may be applicable also to inhibitors of other galectins.

Potential Therapeutic Use of Galectin-3 Inhibitors.

Galectin-3 has been implicated in diverse phenomena and, hence, inhibitors may have multiple uses. It is easy to perceive this as a lack of specificity or lack of scientific focus. Therefore, the analogy with aspirin and the cyclooxygenases (COX-I and II) is useful. The COXs produce the precursor of a wide variety of prostaglandins and, hence, are involved in a diverse array of biological mechanisms. Their inhibitors, aspirin and other NSAIDs (non-steroid anti-inflammatory drugs), also have broad and diverse effects. Despite this, these inhibitors are very useful medically, and they have several different specific utilities.

So if galectins, like COXs, are part of some basic biological regulatory mechanism (as yet unknown), they are likely to be 'used by nature' for different purpose in different contexts. Galectin inhibitors, like NSAIDs, are not expected to wipe out the whole system, but to tilt the balance a bit.

Inhibition of Inflammation.

A pro-inflammatory role of galectin-3 is indicated by its induction in cells at inflammatory sites, a variety of effects on immune cells (e.g. oxidative burst in neutrophils, chemotaxis in monocytes), and decrease of the inflammatory response, mainly in neutrophils and macrophages, in null mutant mice (chapters by Rabinovich et al., Sato et al., and Almkvist et al. in Leffler (editor), 2004b). In particular, macrophage differentiation and fibrosis was recently shown to depend on galectin-3 and galectin-3 inhibitors were demonstrated to block macrophage differentiation and fibrosis-related molecular processes. (Mackinnon et al. 2008) Moreover, knock-out mice of Mac-2BP, a galectin-3 ligand, have increased inflammatory responses (Trahey et al., 1999). Inflammation is a protective response of the body to invading organisms and tissue injury. However, if unbalanced, frequently it is also destructive and occurs as part of the pathology in many diseases. Because of this, there is great medical interest in pharmacological modulation of inflammation. A galectin-3 inhibitor is expected to provide an important addition to the arsenal available for this.

Treatment of Septic Shock.

The idea of a possible role of galectin-3 in septic shock comes from our own studies (Almquist et al., 2001). Briefly, the argument goes as follows. It is known that septic shock involves dissemination of bacterial lipopolysaccharide into the blood stream, and that the pathological effects of this are mediated via neutrophil leukocytes (Karima et al., 1999). LPS does not activate the tissue-damaging response of the neutrophil. Instead, it primes the neutrophil, so that it is converted from unresponsive to responsive to other, presumably endogenous, activators. In septic shock, this priming happens prematurely in the blood stream. Endogenous activators could then induce the tissue damaging response in the wrong place and time. Several candidates have been proposed as these endogenous activators, including TNF-alfa. Inhibitors of these have been used in treatment schemes without much success (Karima et al., 1999). Since our own studies indicate that galectin-3 is a good candidate for being an endogenous activator of primed neutrophils (Almquist et al., 2001), galectin-3 inhibitors may be very useful in septic shock.

Treatment of Cancer.

A large number of immunohistochemical studies show changed expression of certain galectins in cancer (van den Brule et. al. and Bidon et al. in Leffler (editor), 2004b) Galectin-3 is now an established histochemical marker of thyroid cancer, and neoexpression of galectin-4 is a promising marker of early breast cancer (Huflejt and Leffler, 2004). The direct evidence for a role of galectin-3 in cancer comes from mouse models, mainly by Raz et al, but also others (Takenaka et al. in Leffler (editor), 2004b). In paired tumor cell lines (with decreased or increased expression of galectin-3), the induction of galectin-3 gives more tumors and metastasis and suppression of galectin-3 gives less tumors and metastasis. Galectin-3 has been proposed to enhance tumor growth by being anti-apoptotic, promote angiogenesis, or to promote metastasis by affecting cell adhesion. From the above it is clear that inhibitors of galectin-3 might have valuable anticancer effects. Indeed, saccharides claimed but not proven to inhibit galectin-3 have been reported to have anti-cancer effects. In our own study a fragment of galectin-3 containing the CRD inhibited breast cancer in a mouse model by acting as a dominant negative inhibitor (John et al., 2003). Furthermore, galectin inhibitors at nanomolar concentrations decreases tumor cell motility drastically and thus potentially increase sensitivity to conventional cytostatica.

Also galectin-1 is frequently over-expressed in low differentiated cancer cells, and galectin-9 or its relatives galectin-4 and galectin-8 may be induced in specific cancer types (Huflejt and Leffler, 2004; Leffler (editor), 2004b). Galectin-1 induces apoptosis in activated T-cells and has a remarkable immunosuppressive effect on autoimmune disease in vivo (Rabinovich et al; and Pace et al. in Leffler (editor), 2004b. Therefore, the over-expression of these galectins in cancers might help the tumor to defend itself against the T-cell response raised by the host (Rubinstein et al., 2004).

Null mutant mice for galectins-1 and -3 have been established many years ago (Poirier, 2002). These are healthy and reproduce apparently normally in animal house conditions. However recent studies have revealed subtle phenotypes in function of neutrophils and macrophages (as described above) and in bone formation for galectin-3 null mutants, and in nerve and muscle cell regeneration/differentiation for the galectin-1 null mutants (Leffler et al., 2004; Poirier, 2002; Watt in Leffler (editor), 2004b). Recently galectin-7 and galectin-9 null mutant mice have been generated and are also grossly healthy in animal house conditions, but have not yet been analyzed in detail. The differences in site of expression, specificity and other properties make it unlikely that different galectins can replace each other functionally. The observations in the null mutant mice would indicate that galectins are not essential for basic life supporting functions as can be observed in normal animal house conditions. Instead they may be optimizers of normal function and/or essential in stress conditions not found in animal house conditions. The lack of strong effect in null mutant mice may make galectin inhibitors more favorable as drugs. If galectin activity contributes to pathological conditions as suggested above but less to normal conditions, then inhibition of them will have less unwanted side effects.

Known Inhibitors

Natural Ligands.

Solid phase binding assays and inhibition assays have identified a number of saccharides and glycoconjugates with the ability to bind galectins (reviewed by Leffler, 2001 and Leffler et al., 2004). All galectins bind lactose with a $K_d$ of 0.5-1 mM. The affinity of D-galactose is 50-100 times lower. N-Acetyllactosamine and related disaccharides bind about as well as lactose, but for certain galectins, they can bind either worse or up to 10 times better. The best small saccharide ligands for galectin-3 were those carrying blood group A-determinants attached to lactose or lacNAc-residues and were found to bind up to about 50 times better than lactose. Galectin-1 shows no preference for these saccharides.

Larger saccharides of the polylactosamine type have been proposed as preferred ligands for galectins. In solution, using polylactosamine-carrying glycopeptides, there was evidence for this for galectin-3, but not galectin-1 (Leffler and Barondes, 1986). A modified plant pectin polysaccharide has been reported to bind galectin-3 (Pienta et al., 1995).

The above-described natural saccharides that have been identified as galectin-3 ligands are not suitable for use as active components in pharmaceutical compositions, because they are susceptible to acidic hydrolysis in the stomach and to enzymatic degradation. In addition, natural saccharides are hydrophilic in nature, and are not readily absorbed from the gastrointestinal tract following oral administration.

Synthetic Inhibitors.

Saccharides coupled to amino acids with anti-cancer activity were first identified as natural compounds in serum, but subsequently, synthetic analogues have been made (Glinsky et al., 1996). Among them, those with lactose or Gal coupled to the amino acid inhibit galectins, but only with about the same potency as the corresponding underivatized sugar. A chemically modified form of citrus pectin (Platt and Raz, 1992) that inhibits galectin-3 shows anti-tumor activity in vivo (Pienta et al., 1995; Nangia-Makker et al., 2002).

A divalent form of a lactosyl-amino acid had higher potency in a solid phase assay (Naidenko et al., 2000; Huflejt et al., 2001; Huflejt and Leffler, 2004) and clusters having up to four lactose moieties showed a strong multivalency effect when binding to galectin-3, but not to galectin-1 and -5 (Vrasidas et al., 2003). Cyclodextrin-based glycoclusters with seven galactose, lactose, or N-acetyllactosamine residues also showed a strong multivalency effect against galectin-3, but less so against galectins-1 and -7 (André et al., 2004). Starburst dendrimers (André et al., 1999) and glycopolymers (Pohl et al., 1999; David et al., 2004), made polyvalent in lactose-residues, have been described as galectin-3 inhibitors with marginally improved potency as compared to lactose. The aforementioned synthetic compounds that have been identified as galectin-3 ligands are not suitable for use as active components in pharmaceutical compositions, because they are hydrophilic in nature and are not readily absorbed from the gastrointestinal tract following oral administration.

Natural oligosaccharides, glycoclusters, glycodendrimers, and glycopolymers described above are too polar and too large to be absorbed and in some cases are large enough to produce immune responses in patients. Furthermore, they are susceptible to acidic hydrolysis in the stomach and to enzymatic hydrolysis. Thus, there is a need for small synthetic molecules Thiodigalactoside is known to be a synthetic and hydrolytically stable, yet polar inhibitor, approximately as efficient as N-acetyllactosamine (Leffler and Barondes, 1986). A library of pentapeptides provided inhibitors against galectin-1 and -3, but only with low affinities, similar to that of galactose (Arnusch et al., 2004). Furthermore, peptides are not ideal agents for targeting galectins in vivo, as they are susceptible to hydrolysis and are typically polar. N-Acetyllactosamine derivatives carrying aromatic amides or substituted benzyl ethers at C-3" have been demonstrated to be highly efficient inhibitors of galectin-3, with unprecedented $IC_{50}$ values as low as 4.8 µM, which is a 20-fold improvement in comparison with the natural N-acetyllactosamine disaccharide (Sörme et al., 2002; Sörme et al., 2003b). These derivatives are less polar overall, due to the presence of the aromatic amido moieties and are thus more suitable as agents for the inhibition of galectins in vivo. Furthermore, C3-triazolyl galactosides have been demonstrated to be as potent inhibitors as the corresponding C3-amides of some galectins. Hence, any properly structured galactose C3-substituent may confer enhanced galectin affinity.

However, said C3-amido- and C3-triazolyl-derivatised compounds are still susceptible to hydrolytic degradation in vivo, due to the presence of a glycosidic bond in the galactose and N-acetyllactosamine saccharide moiety and, although they are potent small molecule inhibitors of galectin-3, even further improved affinity and stability is desirable. Accordingly, inhibitors based on 3,3'-derivatization of thiodigalactoside have been developed, (Cumpstey et al., 2005; Cumpstey et al., 2008) which lack β-glycosidic hydrolytically and enzymatically labile linkages. These inhibitors also displayed superior affinity for several galectins (down to Kd in the low nM range). Nevertheless, although displaying high affinity for galectins, the 3,3'-derivatized thiodigalactosides still comprise of two galactose monosaccharide moieties that are too polar, resulting in poor absorption and rapid clearance, and too susceptible to enzymatic degradation.

Compounds of the prior art are known by the general formulas

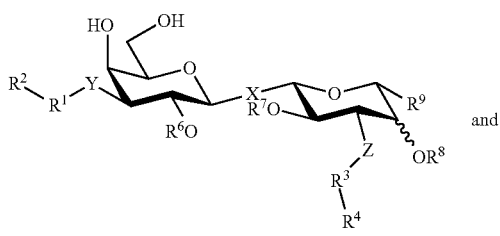

and

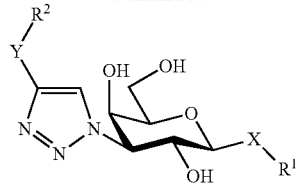

in which second formula $R^1$ can be a D-galactose

Thus, due to the less than optimal pharmacokinetic properties of the compounds of the prior art, there is still a considerable need within the art of inhibitors against galectins, in particular of galectin-1 and galectin-3.

SUMMARY OF THE INVENTION

Therefore the present invention relates to a compound having the general formula (I):

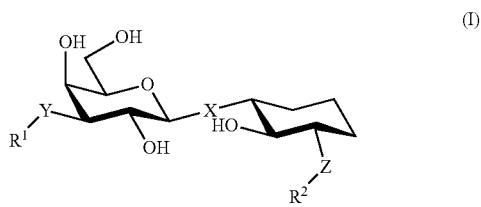

(I)

wherein
the configuration of the pyranose ring is D-galacto;
X is selected from the group consisting of O, S, and SO;
Y and Z are independently selected from being CONH or a 1H-1,2,3-triazole ring;
$R^1$ and $R^2$ are independently selected from the group consisting of:
  a) an alkyl group of at least 4 carbons, an alkenyl group of at least 4 carbons, an alkynyl group of at least 4 carbons;
  b) a carbamoyl group, a carbamoyl group substituted with an alkyl group, a carbamoyl group substituted with an alkenyl group, a carbamoyl group substituted with an alkynyl group, a carbamoyl group substituted with an aryl group, a carbamoyl group substituted with an substituted alkyl group, and a carbamoyl group substituted with an substituted aryl group;
  c) a phenyl group substituted with at least one carboxy group, a phenyl group substituted with at least one halogen, a phenyl group substituted with at least one alkyl group, a phenyl group substituted with at least one alkoxy group, a phenyl group substituted with at least one trifluoromethyl group, a phenyl group substituted with at least one trifluoromethoxy group, a phenyl group substituted with at least one sulfo group, a phenyl group substituted with at least one hydroxy group, a phenyl group substituted with at least one carbonyl group, and a phenyl group substituted with at least one substituted carbonyl group;
  d) a naphthyl group, a naphthyl group substituted with at least one carboxy group, a naphthyl group substituted with at least one halogen, a naphthyl group substituted with at least one alkyl group, a naphthyl group substituted with at least one alkoxy group, a naphthyl group substituted with at least one sulfo group, a naphthyl group substituted with at least one hydroxy group, a naphthyl group substituted with at least one carbonyl group, and a naphthyl group substituted with at least one substituted carbonyl group;

e) a heteroaryl group, a heteroaryl group substituted with at least one carboxy group, a heteroaryl group substituted with at least one halogen, a heteroaryl group substituted with at least one alkoxy group, a heteroaryl group substituted with at least one sulfo group, a heteroaryl group substituted with at least one arylamino group, a heteroaryl group substituted with at least one hydroxy group, a heteroaryl group substituted with at least one halogen, a heteroaryl group substituted with at least one carbonyl group, and a heteroaryl group substituted with at least one substituted carbonyl group; and f) a thienyl group, a thienyl group substituted with at least one carboxy group, a thienyl group substituted with at least one halogen, a thienyl thienyl group substituted with at least one alkoxy group, a thienyl group substituted with at least one sulfo group, a thienyl group substituted with at least one arylamino group, a thienyl group substituted with at least one hydroxy group, a thienyl group substituted with at least one halogen, a thienyl group substituted with at least one carbonyl group, and a thienyl group substituted with at least one substituted carbonyl group.

The present invention also relates to methods of treatment of galectin protein disorders in mammals, in particular humans, wherein a therapeutically effective amount of the compound according to the invention is administered to a mammal in need of the treatment. This treatment may result in inhibition of conditions associated with the binding of galectin to ligands in a mammal.

The present invention further relates to the use of the compounds according to the invention as medicaments as well as to pharmaceutical compositions comprising the compound according to the invention. Such pharmaceutical compositions normally also comprises one or more ingredients selected from the group consisting of pharmaceutically acceptable adjuvants, diluents, excepients and carriers. These medicaments and pharmaceutical compositions are suitable for treatment of any disorder relating to the binding of a galectin to ligands in a mammal.

It is possible to use only one compound according to the invention for the purposes discussed above. It is however also possible to use two or more compounds in combination.

Still further, the present invention relates to a method for inhibiting conditions associated with the binding of galectin to ligands in a mammal, which method comprises administering to said mammal an effective amount of a pharmaceutical composition mentioned above.

Galectin Specificity

The studies of galectin specificity using inhibition by small natural saccharides mentioned above indicated that all galectins bound lactose, LacNAc and related disaccharides, but that galectin-3 bound certain longer saccharides much better (Leffler and Barondes, 1986). These longer saccharides were characterized by having an additional sugar residue added to the C-3 position of Gal in lactose or LacNAc. The X-ray crystal structures of galectins-1, -2, and -3 demonstrated a highly conserved core binding site for lactose and LacNAc with features in agreement with the specificity studies (Lobsanov and Rini, 1997; Seetharaman et al., 1998). In addition, an extended groove was found, which might accommodate the added sugar residue in the longer saccharides (A-B in FIG. 1). The shape of this groove varies between galectins, suggesting that the same extensions would not be bound equally by the different galectins. Moreover, including additional galectins (e.g. galectins-4, -8 and -9) it has become clear that there is also variations in binding preference on the other side of the Gal residue (sites D-E in FIG. 1)(Leffler et al., 2004).

Design of triazolyl- and Amido-Substituted Cyclohexyl Galactosides as Galectin Inhibitors.

The extended binding site close to HO-3' of N-acetyllactosamine (site B, FIG. 1b) has been exploited in the design of potent galectin-3-inhibiting 3'-amido-N-actyllactosamine derivatives. (Sörme et al., 2002) In particular, aromatic amides or substituted triazole rings at C3 of galactopyranose-containing compounds made efficient inhibitors (Salameh et al., 2005; Sörme et al., 2005) by forming an energetically favorable stacking interaction with the arginine-144 guanidino group of galectin-3. (Sörme et al., 2005) Furthermore, it was demonstrated that The presence of additional arginine residues in or close to the N-acetyllactosamine/lactose binding site of galectins suggested the design of inhibitors that make use of additional stacking interactions between aromatic groups and arginine guanidino groups to provide even more potent inhibitors. For example, the N-acetyl group of N-acetyllactosamine is, according the crystal structure of galectin-3 in complex with N-acetyllactosamine, interacting with arginine-186 of galectin-3 (FIG. 1b). Replacing said N-acetyl group with an aromatic amido group would allow for a new stacking interaction between the aromatic amide and the arginine 186 guanidino group or with the corresponding conserved arginine residues in other galectins.

Furthermore, replacing the N-acetyllactosamine disaccharide with a hydrolytically stable mimic would add value to an inhibitor in terms of longer half-life in vivo. Thiodigalactoside was used as such a hydrolytically stable N-acetyllactosamine mimic, which is believed to bind to galectins in a manner mimicking that of N-acetyllactosamine. As N-acetyllactosamine derivatives carrying aromatic amido groups at C-3' show high affinity for galectin-3 due to an interaction with arginine-144, symmetrical thiodigalactoside derivatives carrying aromatic amides at both C-3 carbons allowed for the formation of an arene-guanidino interaction between one of the aromatic amido groups and arginine 144 (analogous to the interaction with the 3"-amido-N-acetyllactosamine derivative). The second aromatic amido group is positioned similarly to the N-acetyl group of N-acetyllactosamine, i.e. close to arginine-186 upon binding to galectin-3; that would be in site D as shown in FIG. 1a. Henceforth, symmetrical thiodigalactoside derivatives with aromatic amides at both C-3 carbons were demonstrated to particularly potent inhibitors of several members of the galectin family of proteins with Kd values down to the low nM range (Cumpstey et al. 2005; Cumpstey et al. 2008). Nevertheless, although displaying high affinity for galectins, the 3,3'-derivatized thiodigalactosides still comprise of two galactose monosaccharide moieties that are too polar, resulting in poor absorption and rapid clearance, and too susceptible to enzymatic degradation.

An approach towards less polar and more stable galectin inhibitors would be to replaced one or more carbohydrate residues of the inhibitors with non-saccharide structural moieties. A cyclohexane ring is such a conceptually simple pyranose mimicking structural moiety. However, if a subsite D-binding N-acetylglucosamine residue of N-acetyllactosamine is to be replaced by a cyclohexane ring, said cyclohexane ring should preferably carry a hydroxyl group capable of taking part in key hydrogen bonds (e.g. with arg162 and glu184 in galectin-3) and a substituted triazole or amide capable of interacting with conserved galectin arginine sidechains.

DETAILED DESCRIPTION OF THE PREFERRED EMBODIMENTS OF THE INVENTION

Figure 1A:
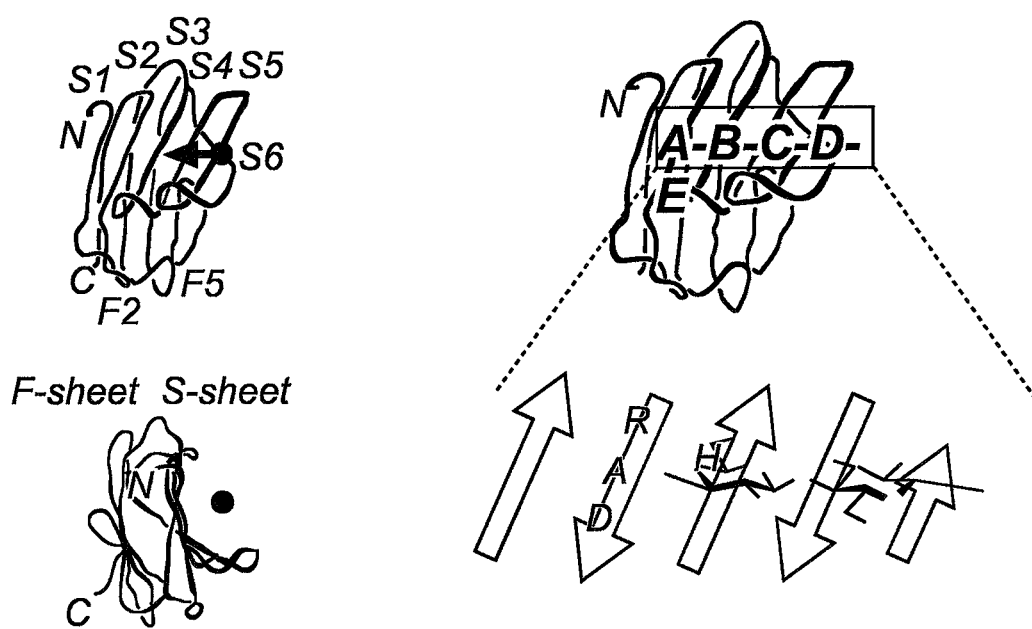
FIG. 1. a) Schematic of the galectin carbohydrate recognition domain (CRD)(left) and carbohydrate binding sites (right)(Barondes et al., 1994; Leffler et al., 2004). The CRD is shown in face and side view with bound disaccharide symbolized by arrow or dot (left). It consists of two β-sheets named S and F. The concave side of the S-sheets forms a groove that can hold about a tetrasaccharide and has four subsites (A-D) with the defining galactose binding site as C, and a fifth subsite (E) outside the groove (top right). A bound LacNAc is shown on the S-beta sheet (bottom right) with extensions into subsite B and E. Pertinent amino acids in galectin-3 around subsite B are indicated in one letter code (grey).
FIG. 1b) Structure of carbohydrate recognition site of galectin-3 CRD (smooth surface) with bound LacNAc (stick model). The subsites described in FIG. 1a are indicated below the figure with Gal in site C. The arrows indicate spaces in site B targeted by derivatization on position 3 of the Gal (Sörme et al., 2002). Selected amino acids are named. The GlcNAc of the LacNAc is in site D.
Figure 1B:
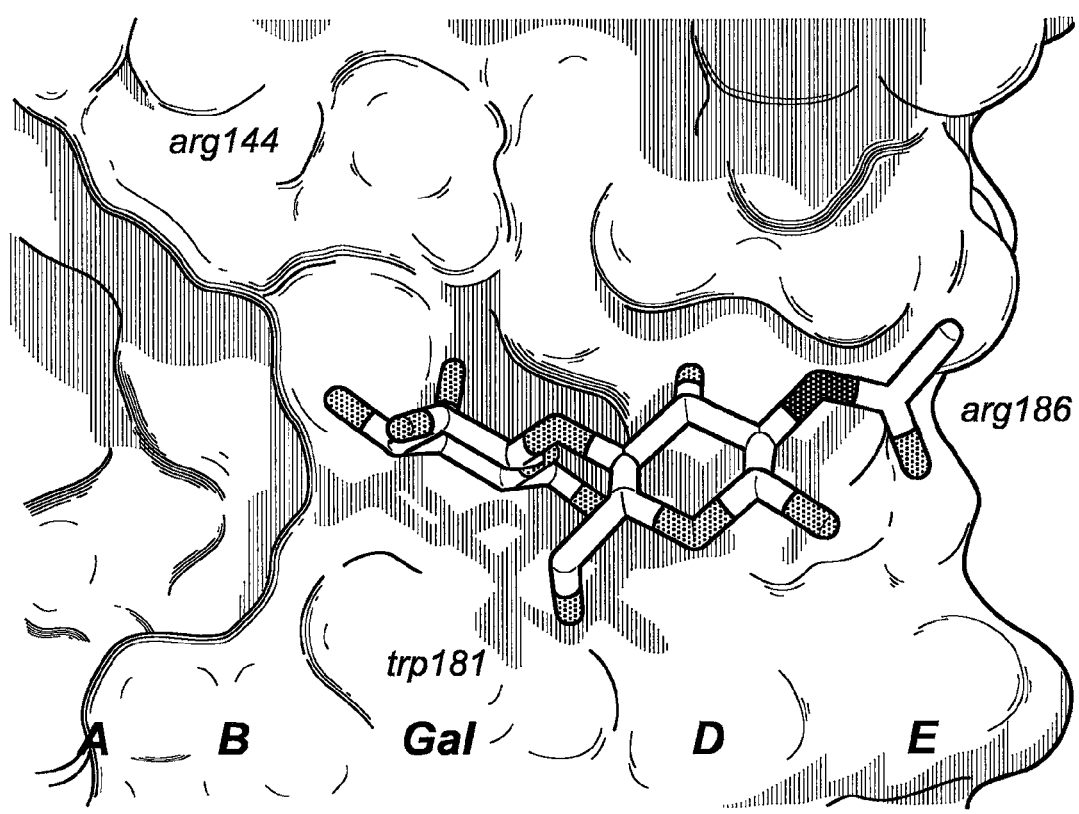
Figure 2:
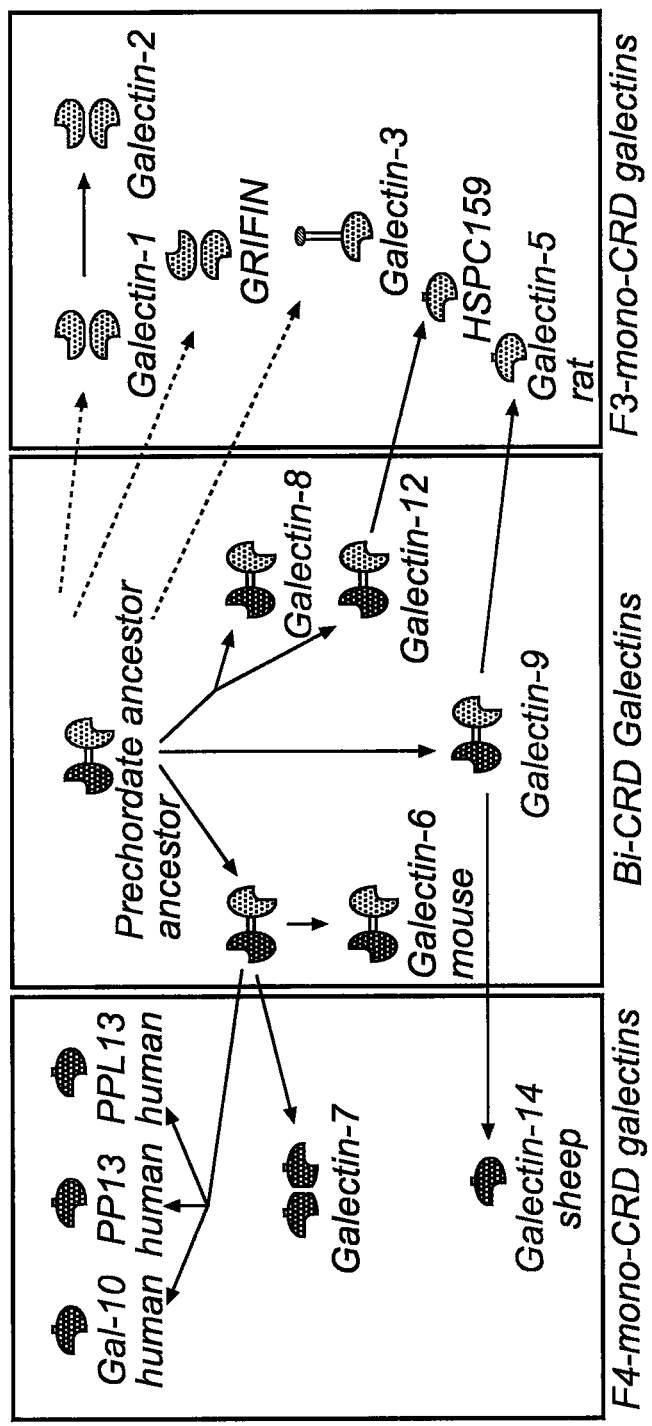
FIG. 2. Mammalian galectins and their phylogeny from a prechordate ancestor (Houzelstein et al., 2004). All the CRDs are of either of two types (F4 and F3, black and grey respectively) defined by corresponding gene structure (intron-exon boundaries) and supported by their respective sequence relationships. The ancestral prechordate galectins include a bi-CRD galectin with one of each CRD type (most likely derived in much earlier evolution from duplication of a mono-CRD galectin). Large scale duplication of genome fragments in early chordate-vertebrate evolution give rise to the four major bi-CRD galectins found in mammals. Local duplication-deletion events give rise to mono-CRD galectins related to either the N- or C-terminal CRD. Some of these occurred at early more uncertain times (dotted arrows) whereas other are recent and more certain (filled arrows). Recent duplications have also produced extra copies of bi-CRD galectins in certain mammals (e.g. two extra copies of galectin-9s in humans (not shown); galectin-6 in mouse).

According to one aspect of the invention, in the above-mentioned formula, X is S or O.

According to one aspect of the invention Y and Z may both be either CONH or a 1H-1,2,3-triazole ring. Furthermore, Y may be CONH when Z is a 1H-1,2,3-triazole ring, and Y may be a 1H-1,2,3-triazole ring when Z is CONH, When Y is CONH the CONH group may be linked via the N atom to the pyranose ring.

When Y is a 1H-1,2,3-triazole ring it may be is linked via the N1 atom to the pyranose ring. In this case, $R^1$ may be linked to the C4 atom of the 1H-1,2,3-triazole ring.

When Z is CONH the CONH group may be linked via the N atom to the cyclohexane.

When Z is a 1H-1,2,3-triazole ring it may be is linked via the N1 atom to the cyclohexane. In this case, $R^2$ may be linked to the C4 atom of the 1H-1,2,3-triazole ring.

According to one aspect of the invention, $R^1$ and $R^2$ are independently selected from the group consisting of a carbamoyl group, an alkylated carbamoyl group, an alkenylated carbamoyl group, an arylated carbamoyl group, a phenyl group, a substituted phenyl group, a halogenated phenyl group, a fluorinated phenyl group, a chlorinated phenyl group, a brominated phenyl group, an alkylated phenyl group, an alkenylated phenyl group, a trifluoromethylated phenyl group, a methoxylated phenyl group, a trifluoromethoxylated phenyl group, a naphthyl group, a substituted naphthyl group, a heteroaryl group, a substituted heteroaryl group, a thienyl group, and a substituted thienyl group.

According to another aspect either one of or both of $R^1$ and $R^2$ may be selected from the group consisting of an alkylated carbamoyl group, a fluorinated phenyl group, and a thienyl group.

In the present disclosure, the term "alkylated" means that the group is substituted with an alkyl group. the term "alkenylated" means that the group is substituted with an alkenyl group "alkenyl group" etc.

The term "alkyl group" is meant to comprise from 1 to 7 carbon atoms, preferably 1 to 4 carbon atoms. Said alkyl group may be straight- or branched-chain. Said alkyl group may also form a cycle comprising from 3 to 7 carbon atoms, preferably 3, 4, 5, 6, or 7 carbon atoms. Thus alkyl will mean any of methyl, ethyl, n-propyl, isopropyl, n-butyl, sec-butyl, tert-butyl, pentyl, isopentyl, 3-methylbutyl, 2,2-dimethylpropyl, n-hexyl, 2-methylpentyl, 2,2-dimethylbutyl, 2,3-dimethylbutyl, n-heptyl, 2-methylhexyl, 2,2-dimethylpentyl, 2,3-dimethylpentyl, cyclopropyl, cyclobutyl, cyclopentyl, cyclohexyl, cycloheptyl, and 1-methylcyclopropyl.

In the present disclosure, the term "alkenyl group" is meant to comprise from 2 to 7 carbon atoms. Said alkenyl group comprises at least one double bond. Thus alkenyl group will mean any of vinyl, allyl, but-1-enyl, but-2-enyl, 2,2-dimethylethenyl, 2,2-dimethylprop-1-enyl, pent-1-enyl, pent-2-enyl, 2,3-dimethylbut-1-enyl, hex-1-enyl, hex-2-enyl, hex-3-enyl, prop-1,2-dienyl, 4-methylhex-1-enyl, cycloprop-1-enyl group, and others.

In the present disclosure the term "aryl group" is meant to comprise from 4 to 12 carbon atoms. Said aryl group may be a phenyl group or a naphthyl group. The above-mentioned groups may naturally be substituted with any other known substituents within the art of organic chemistry. The groups may also be substituted with two or more of the said substituents. Examples of substituents are halogen, alkyl, alkenyl, alkoxy, nitro, sulfo, amino, hydroxy, and carbonyl groups. Halogen substituents are bromo, fluoro, iodo, and chloro. Alkyl groups are as defined above containing 1 to 7 carbon atoms. Alkenyl are as defined above containing 2 to 7 carbon atoms, preferably 2 to 4. Alkoxy is as defined below containing 1 to 7 carbon atoms, preferably 1 to 4 carbon atoms, which may contain an unsaturated carbon atom. Combinations of substituents can be present such as trifluoromethyl.

In the present disclosure, the term "alkoxy group" is meant to comprise from 1 to 7 carbon atoms, preferably 1 to 4 carbon atoms. Said alkoxy group may be a methoxy group, an ethoxy group, a propoxy group, a isopropoxy group, a n-butoxy group, a sec-butoxy group, tert-butoxy group, pentoxy group, isopentoxy group, 3-methylbutoxy group, 2,2-dimethylpropoxy group, n-hexoxy group, 2-methylpentoxy group, 2,2-dimethylbutoxy group 2,3-dimethylbutoxy group, n-heptoxy group, 2-methylhexoxy group, 2,2-dimethylpentoxy group, 2,3-dimethylpentoxy group, cyclopropoxy group, cyclobutoxy group, cyclopentyloxy group, cyclohexyloxy group, cycloheptyloxy group, and 1-methylcyclopropyl oxy group In the present disclosure, the term "alkylamino group" is meant to comprise from 1 to 7 carbon atoms, preferably 1 to 4 carbon atoms, wherein the alkyl group is as defined above. Thus alkyl will mean any of methyl, ethyl, n-propyl, isopropyl, n-butyl, sec-butyl, tert-butyl, pentyl, isopentyl, 3-methylbutyl, 2,2-dimethylpropyl, n-hexyl, 2-methylpentyl, 2,2-dimethylbutyl, 2,3-dimethylbutyl, n-heptyl, 2-methylhexyl, 2,2-dimethylpentyl, 2,3-dimethylpentyl, cyclopropyl, cyclobutyl, cyclopentyl, cyclohexyl, cycloheptyl, and 1-methylcyclopropyl.

In the present disclosure, the term "arylamino group" is meant to comprise from 4 to 7 carbon atoms. Said "arylamino group" may be aniline, carboxylated aniline or halogenated aniline, halogen being as defined above.

In the present disclosure, the term "aryloxy group" is meant to comprise from 4 to 12 carbon atoms. Said "aryloxy group" may be phenol, carboxylated phenol or halogenated phenol, wherein halogen is as defined above.

In the present disclosure, the term "heteroaryl group" is meant to comprise any aryl group comprising from 4 to 18 carbon atoms, wherein at least one atom of the ring is a heteroatom, i.e. not a carbon. Preferably, said heteroatom is N, O or S. Said heteroaryl group may be a pyridine, or an indole group.

The above-mentioned groups may be substituted with any other known substituents within the art of organic chemistry. The groups may also be substituted with two or more of the substituents. Examples of substituents are halogen, alkoxy, nitro, sulfo, amino, hydroxy, and carbonyl groups. Halogen substituents are bromo, fluoro, iodo, and chloro. Alkyl groups are as defined above containing 1 to 7 carbon atoms. Alkenyl are as defined above containing 2 to 7 carbon atoms, preferably 2 to 4. Alkoxy is as defined below containing 1 to 7 carbon atoms, preferably 1 to 4 carbon atoms, which may contain an unsaturated carbon atom.

In one aspect of the invention, the compound is selected from the group consisting of:
((1R,2R,3S)-2-hydroxy-3-(4-(N-(1-propyl)-carbamoyl)-1H-1,2,3-triazol-1-yl)cyclohexyl) 3-deoxy-(3-(4-(N-(1-propyl)-carbamoyl)-1H-1,2,3-triazol-1-yl))-β-D-galactopyranoside (7),
((1R,2R,3S)-2-hydroxy-3-(4-(2-fluorophenyl)-1H-1,2,3-triazol-1-yl)-cyclohexyl) 3-deoxy-3-(4-(2-fluorophenyl)-1H-1,2,3-triazol-1-yl)-1-thio-β-D-galactopyranoside (15),
((1R,2R,3S)-2-hydroxy-3-(4-(3-fluorophenyl)-1H-1,2,3-triazol-1-yl)-cyclohexyl) 3-deoxy-3-(4-(3-fluorophenyl)-1H-1,2,3-triazol-1-yl)-1-thio-β-D-galactopyranoside (16),
((1R,2R,3S)-2-hydroxy-3-(4-(4-fluorophenyl)-1H-1,2,3-triazol-1-yl)-cyclohexyl) 3-deoxy-3-(4-(4-fluorophenyl)-1H-1,2,3-triazol-1-yl)-1-thio-β-D-galactopyranoside (17),
(1R,2R,3S)-2-hydroxy-3-(4-(3-thienyl)-1H-1,2,3-triazol-1-yl)-cyclohexyl) 3-deoxy-3-(4-(3-thienyl)-1H-1,2,3-triazol-1-yl)-1-thio-β-D-galactopyranoside (18),
(1R,2R,3S)-2-hydroxy-3-(4-(N-(1-propyl)-carbamoyl)-1H-1,2,3-triazol-1-yl)-cyclohexyl) 3-deoxy-3-(4-(N-(1-propyl)-carbamoyl)-1H-1,2,3-triazol-1-yl)-1-thio-β-D-galactopyranoside (19), and
(1R,2R,3S)-2-hydroxy-3-(4-chlorobenzamido)-cyclohexyl) 3-deoxy-3-(4-chlorobenzamido)-1-thio-β-D-galactopyranoside (22).

In one aspect, the present invention relates to the use of a compound according to the above-mentioned formula for the manufacture of a medicament for the treatment of any disorder relating to the binding of a galectin to receptors in a mammal. In one aspect of the invention, said galectin is galectin-3.

In another aspect, the invention relates to the use of a compound according to the above-mentioned formula for the manufacture of a medicament for the treatment of a disorder being selected from the group consisting of inflammation, septic shock, cancer, and autoimmune diseases such as rheumatoid arthritis and multiple sclerosis. Preferably, said compound is for the manufacture of a medicament for the treatment of cancer.

In yet another aspect, the present invention relates to a pharmaceutical composition comprising a compound according to the above-mentioned formula as active ingredient together with a pharmaceutically acceptable adjuvant, diluent, excepient or carrier. A pharmaceutical composition of the invention comprises from 1 to 99 weight % of a pharmaceutically acceptable adjuvant, diluent, excepient or carrier and from 1 to 99 weight % of a compound according to above mentioned formula.

In one aspect, the invention relates to a method for inhibiting conditions associated with the binding of galectin to receptors in a mammal which method comprises administering to said mammal, an effective amount of a compound according to the above-mentioned formula. In one particularly important aspect of the invention, said galectin is galectin-3.

In another aspect, the invention relates to a method for inhibiting conditions associated with the binding of galectin to receptors in a mammal, which method comprises administering to said mammal an effective amount of a pharmaceutical composition according to the above. In one particularly important aspect of the invention, said galectin is galectin-3.

The pharmaceutical composition according to the present invention comprising a compound of the invention may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition of the present invention may be in the form of, for example, tablets, capsules, powders, solutions, transdermal patches or suppositories.

The pharmaceutical composition of the present invention may optionally comprise two or more compounds of the present invention. The composition may also be used together with other medicaments within the art for the treatment of related disorders.

The typical dosages of the compounds of the present invention vary within a wide range and depend on many factors, such as the route of administration, the requirement of the individual in need of treatment, the individual's body weight, age and general condition.

The adjuvants, diluents, excepients and/or carriers that may be used in the composition of the invention must be pharmaceutically acceptable in the sense of being compatible with the compounds and the other ingredients of the pharmaceutical composition, and not deleterious to the recipient thereof. The adjuvants, diluents, excepients and carriers that may be used in the pharmaceutical composition of the invention are well known to a person within the art.

Synthesis of triazolyl- and Amido-Substituted Cyclohexyl Galactosides

The triazolyl- and amido-substituted cyclohexyl galactosides were synthesized from known (US2008200406) chiral cyclohexen oxide ((1R,2R,6R)-2-(triphenylmethoxy)-7-oxabicyclo[4.1.0]heptane) (1) and methyl 2,4,6-tri-O-acetyl-3-azido-3-deoxy-1-thio β-D galactopyranoside (Sörme et al., 2002) as shown in schemes 1-3.

Scheme 1.
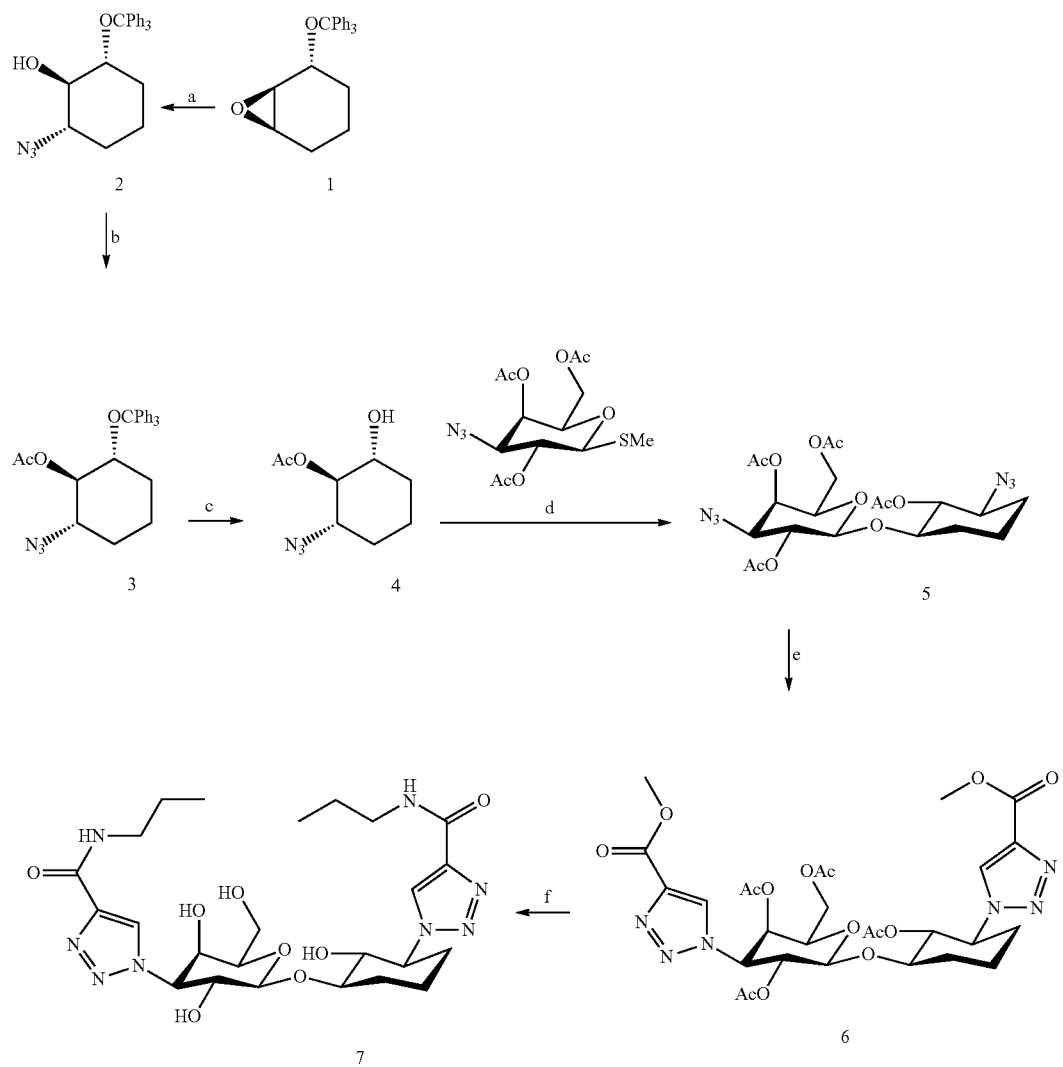
a) NaN₃, H₂O, MeOH (62%); b) AcCl, pyridine, CH₂Cl₂ (100%); c) AcOH (81%)
d) NIS, TfOH, CH₂Cl₂ (6%); e) methylpropiolate, CuI, DIPEA, toluene (44%); f) propylamine, MeOH (53%).
Scheme 2.
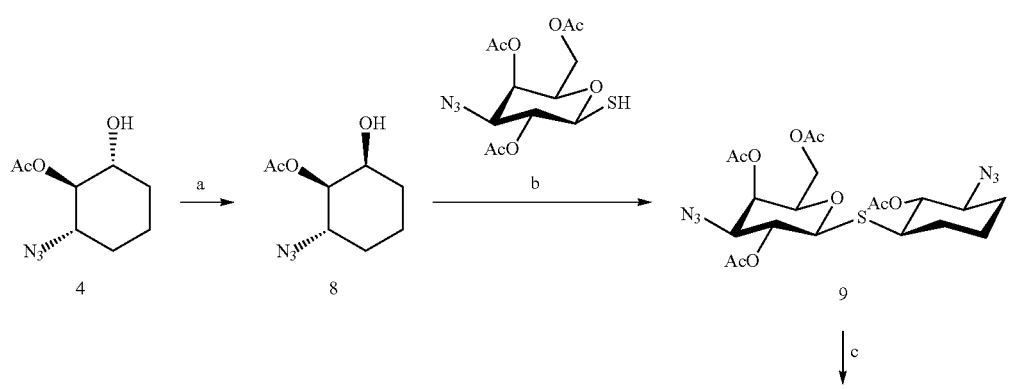

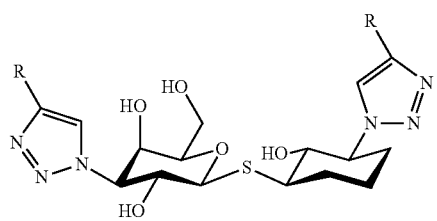
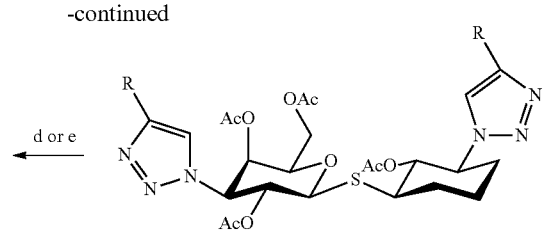

a) $^iTf_2O$, pyridine, $CH_2Cl_2$, $^{ii}Bu_4NNO_2$, DMF (64%); b) $^iTf_2O$, pyri-dine, $CH_2Cl_2$, $^{ii}$2,4,6-tri-O-acetyl-3-azido-3-deoxy-1-thio-β-D-galactopyranoside, $Et_3N$, $CH_2Cl_2$, (43%); c) alkyne (for R see Table 1 below), CuI, DIPEA, toluene (44-93%); d) NaOMe (0.05 M in MeOH) (53-85%); e) n-Propylamine, MeOH.

TABLE 1

R structures of scheme 2

| R in structure of scheme 2 | Alkyne in of scheme 2 | c) yield (%) | d) yield (%) | e) yield (%) |
|---|---|---|---|---|
| Orto-fluorophenyl | 1-ethynyl-orto-fluorobenzene | 93 (10) | 55 (15) | |
| Meta-fluorophenyl | 1-ethynyl-meta-fluorobenzene | 66 (11) | 83 (16) | |
| Para-fluorophenyl | 1-ethynyl-para-fluorobenzene | 44 (12) | 85 (17) | |
| 3-thienyl | 3-ethynyl thiophene | 88 (13) | 53 (18) | |
| N-(1-Propyl)-carbamoyl | Methyl propiolate | 100 (14) | | 68 (19) | erence compounds. Indeed, all compounds were potent inhibitors of galectin-1 and galectin-3 with dissociation constant in the low μM or nM range. This evidences that a properly structured cyclohexane can mimic the subsite D-binding saccharide moiety, e.g. N-acetylglucosamine in the disaccharide N-acetyllactosamine. In particular, substituted (1R,2R,3S)-2-hydroxy-3-(1H-1,2,3-triazol-1-yl)-cyclohexyl) β-D-galactopyranosides and (1R,2R,3S)-2-hydroxy-3-(amido)-cyclohexyl) β-D-galactopyranosides are capable of such mimicking, as are their corresponding thioglycosides. Hence, combining said (1R,2R,3S)-2-hydroxy-3-(1H-1,2,3-triazol-1-yl)-cyclohexyl) β-D-galactopyranosides and (1R,2R,3S)-2-hydroxy-3-(amido)-cyclohexyl) β-D-galactopyranosides with galactose C3 triazoles or aromatic amides results in potent galectin inhibitors several order of magnitude better than know reference inhibitors.

The unexpectedly high inhibitor potency, suitable polarity, and stability of said substituted cyclohexyl galactosides against galectin-3 render them suitable to be active components in pharmaceutical compositions targeting conditions where galectin-3 plays a pathogenic role.

Scheme 3.

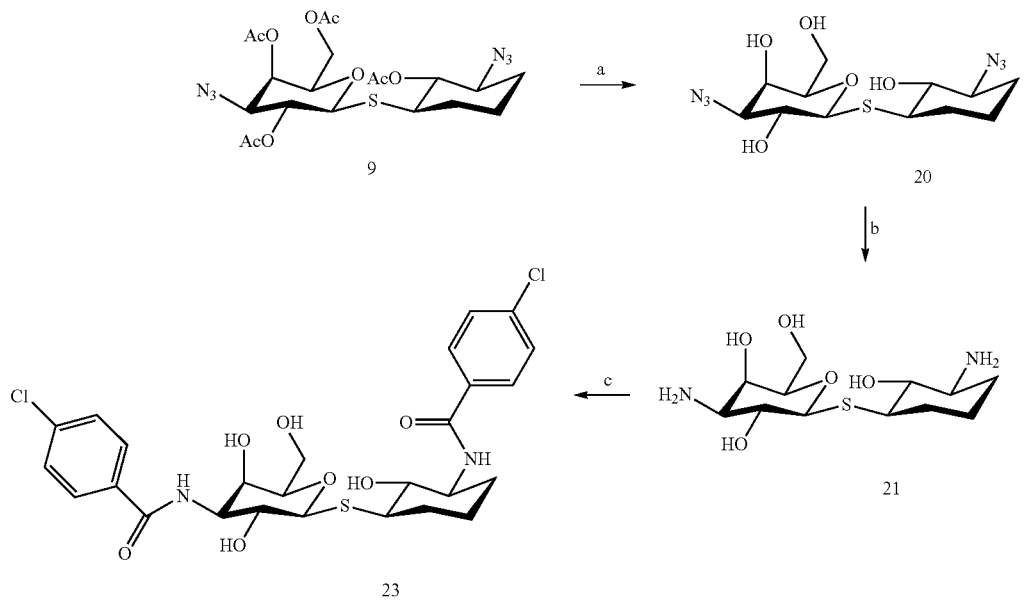

a) NaOMe (0.5M in MeOH); b) $PPh_3$, THF, $H_2O$; c) 4-Chlorobenzoyl chloride, $Na_2CO_3$ (aq., 1M) (16% over three steps from 20).

Evaluation of $K_d$ Values Against Galectin-3

Compounds 7, 15-19, and 22 were evaluated for their efficiency in inhibiting galectin-1 and galectin-3 (Table 2) in a known fluorescence polarization-based assay (Sörme et al., 2003a, 2004). The known galectin inhibitors galactose and N-acetyllactosamine methyl glycosides were included as ref-

TABLE 2

Affinity of compounds for galectin-1 and galectin-3 as calculated from test by fluorescence polarization.

| | Structure | Tested Conc. (μM) Galectin-1 | Calculated K$_d$ (μM) Galectin-1 | Tested Conc. (μM) Galectin-3 | Calculated K$_d$ (μM) Galectin-3 |
|---|---|---|---|---|---|
| Reference Compound | | 20000 | >10000 | 10000 | 4400 |
| Reference Compound | | 200 | 65 | 200 | 59 |
| 7 | 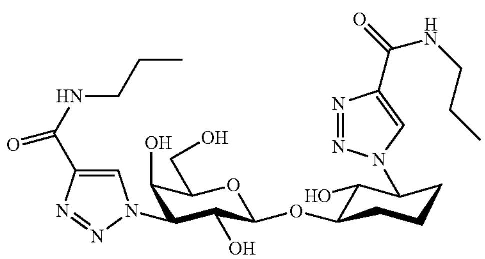 | — | — | 1 | 0.43 |
| 15 | 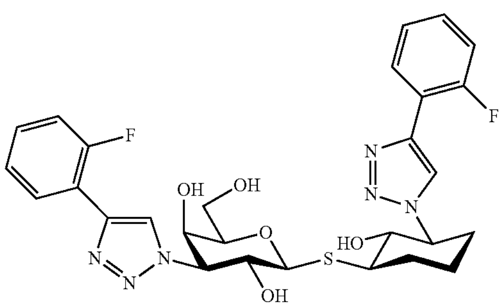 | 2 | 1.9 | 1 | 0.23 |
| 16 | 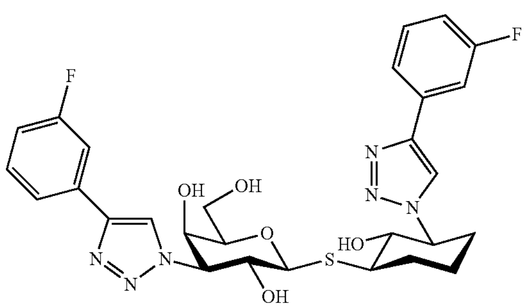 | 2 | 1.5 | 1 | 0.15 |

TABLE 2-continued

Affinity of compounds for galectin-1 and galectin-3 as calculated from test by fluorescence polarization.

| Structure | Tested Conc. (μM) Galectin-1 | Calculated $K_d$ (μM) Galectin-1 | Tested Conc. (μM) Galectin-3 | Calculated $K_d$ (μM) Galectin-3 |
|---|---|---|---|---|
| 17 | 2 | 1.2 | 1 | 0.21 |
| 18 | 2 | 0.35 | 1 | 0.55 |
| 19 | 2 | 1.3 | 0.5 | 0.19 |
| 23 | 10 | 6.3 | 4 | 1.4 |

Methodology/Experimental
General Synthetic Procedures

The compounds of this invention may be prepared by the following general methods and procedures. The galectin-3 assays of this invention may be performed by the following general methods and procedures. It should be appreciated that where typical or preferred process conditions (e.g. reaction temperatures, times, molar ratios of reactants, solvents, pressures, pH etc) are given, other process conditions may also be used unless otherwise stated. Optimum reaction conditions may vary with the particular reactants, solvents used and pH etc., but such conditions can be determined by one skilled in the art by routine optimization procedures.

Identification of the substances was made by HRMS (Micromass Q-tof micro) and NMR (Bruker Ultrashield 400 plus, 400 MHz). Chemical shifts are reported downfield from Me$_4$Si using residual CHD$_2$Cl (7.26 ppm) or CHD$_2$OD (3.35 ppm) as reference. Chemical shifts and coupling constants were obtained from $^1$H-NMR and proton resonances were assigned from COSY experiments. Purification was made by RF-HPLC (Beckman, system gold) or flash chromatography, using silica gel (Davisil 35-70 μm, 60 Å). Reactions were followed by TLC (Aluminum sheet, silica gel 60 F254) observed by UV light, $H_2SO_4$(aq) or a iso-vanillin/$H_2SO_4$/EtOH solution. THF and $Et_2O$ were dried over sodium/benzophenone and distilled. $CH_2Cl_2$ was dried by molecular sieves (4 Å, 1.6 mm). Other solvents and reagents were commercially available and used without further purifications. Fluorescence polarization experiments were performed on a PolarStar instrument (BMG, Offenburg; Germany). Evaluation of 7, 15-19, and 22 as inhibitors of galectins was performed by use of fluorescence polarization as described in the literature (Sörme et al., 2003a, 2004).

(1R,2S,6R)-2-azido-6-(trityloxy)cyclohexanol (2)

The diastereomeric mixture of (1R,2R,6R)-2-(triphenylmethoxy)-7-oxabicyclo[4.1.0]heptane 1 (755 mg, 2.12 mmol) and the S,S-epoxide was dissolved with $NaN_3$ (861 mg, 13.3 mmol) in $H_2O$ (1.7 mL) and MeOH (15 mL). The mixture was heated to 80° C., refluxed over night and then diluted with water and $CH_2Cl_2$. The organic layer was separated and the aqueous layer was rewashed ($CH_2Cl_2$). The entire organic layer was dried ($MgSO_4$), filtered and concentrated. Purification was made by recrystallization in MeOH at −18° C. The reaction yielded 62% of 2. $^1$H-NMR (CDCl$_3$) 7.50 (m, 6 H), 7.20-7.40 (m, 9 H), 3.69 (t, J=9.50 Hz, 1 H), 3.05 (ddd, J=4.80, 9.44, 12.05 Hz, 1 H), 2.91 (ddd, J=4.17, 8.81, 11.28 Hz, 1 H), 2.70 (s, 1 H), 1.80 (m, 1 H), 1.50 (m, 2 H), 1.20-1.40 (m, 2 H), 0.80 (m, 1 H).

(1R,2S,6R)-2-azido-6-(trityloxy)cyclohexyl acetate (3)

Compound 2 (625 mg, 1.57 mmol), pyridine (363 μL, 4.69 mmol) and AcCl (272 μL, 3.13 mmol) were dissolved in $CH_2Cl_2$ (15 mL) under nitrogen atmosphere at room temperature. After 2 h the mixture was diluted with $CH_2Cl_2$. The organic layer was washed (HCl(aq) 5%, sat NaHCO$_3$, brine), dried (MgSO$_4$), filtered and concentrated. No further purification was needed. The reaction yielded 100% of 3. $^1$H-NMR (CDCl$_3$) 7.45 (m, 6 H), 7.20-7.35 (m, 9 H), 5.14 (t, J=9.49 Hz, 1 H), 2.99-3.10 (m, 2 H), 1.93 (s, 3 H), 1.86 (m, 1 H), 1.50 (m, 2 H), 1.25-1.40 (m, 2 H), 0.80 (m, 1 H).

(1R,2S,6R)-2-azido-6-hydroxycyclohexyl acetate (4)

Compound 3 (677 mg, 1.53 mmol) was dissolved in AcOH (10 mL), heated to 56° C. and left over night. The mixture was concentrated and purified by flash chromatography using EtOAc:n-heptan (1:1) as eluent. The reaction yielded 81% of 4. $^1$H-NMR (CDCl$_3$) 4.72 (t, J=9.54 Hz, 1 H), 3.56 (m, 1 H), 3.47 (m, 1 H), 2.19 (s, 3 H), 2.00-2.10 (m, 3 H), 1.80 (m, 1 H), 1.25-1.45 (m, 3 H). HRMS calculated mass ($C_8H_{14}N_3O_3^+$): 200.1030, observed mass: 200.1056.

((1R,2R,3S)-2-acetoxy-3-azidocyclohexyl) 2,4,6-tri-O-acetyl-3-azido-3-deoxy β-D-galactopyranoside (5)

Compound 4 (29.5 mg, 147 μmol), methyl 2,4,6-tri-O-acetyl-3-azido-3-deoxy-1-thio-β-D-galactopyranoside (63.7 mg, 178 μmol) and activated molecular sieves AW300 was stirred under nitrogen at room temperature. for 30 min before it was cooled to −42° C. N-iodosuccinimide (49.5 mg, 221 μmol) and TfOH (1.91 μL, 22.1 μmol) was added. After 4 h the reaction was heated to −18° C. left over night and then heated to room temperature, filtered and diluted with $CH_2Cl_2$. The organic layer was washed (Na$_2$S$_2$O$_3$(aq)), dried (MgSO$_4$), filtered and concentrated. Purification was made by flash chromatography using acetone:toluene (1:10) as eluent. The reaction yielded 6.1% of 5. $^1$H-NMR (CDCl$_3$) 5.42 (dd, J=0.99, 3.40 Hz, 1 H), 5.06 (dd, J=7.75, 10.72 Hz, 1 H), 5.33 (t, J=9.55 Hz, 1 H), 4.48 (d, J=7.82 Hz, 1 H), 4.10 (m, 2 H), 3.85 (dt, J=1.19, 6.71 Hz, 1 H), 3.62 (m, 1 H), 3.54 (dd, J=3.41, 10.65 Hz, 1 H), 3.36 (m, 1 H), 2.19 (s, 3 H), 2.12 (s, 3 H), 2.11 (s, 3 H), 2.08 (s, 3 H), 2.00-2.10 (m, 2 H), 1.81 (m, 1 H), 1.25-1.45 (m, 3 H). HRMS calculated mass ($C_{20}H_{28}N_6NaO_{10}^+$): 535.1759, observed mass: 535.1776.

((1R,2R,3S)-2-acetoxy-3-(4-(methoxycarbonyl)-1H-1,2,3-triazol-1-yl)cyclohexyl) 2,4,6-tri-O-acetyl-3-deoxy-(3-(4-(methoxycarbonyl)-1H-1,2,3-triazol-1-yl)) β-D-galactopyranoside (6)

Compound 5 (8 mg, 15.7 μmol), methylpropionate (2.78 μL, 31.2 μmol), CuI (595 μg, 3.12 μmol) and diisopropylethylamine (5.35 μL, 31.2 μmol) were dissolved in toluene (1 mL), heated to 45° C. and left over night. The mixture was concentrated and purified by flash chromatography using EtOAc as eluent. The reaction yielded 44% of 6. $^1$H-NMR (CDCl$_3$) 8.15 (s, 1 H), 8.14 (s, 1 H), 5.50 (m, 2 H), 5.15-5.20 (m, 2 H), 4.71 (d, J=7.53 Hz, 1 H), 4.65 (m, 1 H), 4.10 (m, 3 H), 3.96 (s, 3 H), 3.95 (s, 3 H), 2.28 (m, 1H), 2.18 (m, 1 H), 2.08 (s, 3 H), 2.06 (s, 3 H), 1.95-2.10 (m, 3 H), 1.91 (s, 6 H), 1.50 (m, 2 H). HRMS calculated mass ($C_{28}H_{36}N_6NaO_{14}^+$): 703.2182, observed mass: 703.2201.

((1r,2r,3s)-2-hydroxy-3-(4-(N-(1-propyl)-carbamoyl)-1h-1,2,3-triazol-1-yl)cyclohexyl) 3-deoxy-(3-(4-(N-(1-propyl)-carbamoyl)-1h-1,2,3-triazol-1-yl))-β-D-galactopyranoside (7)

Compound 6 (5 mg, 7.37 μmol) was dissolved in MeOH: propylamine (5:1, 2.4 mL) and left over night at room temperature. The mixture was concentrated and purified by flash chromatography using MeOH: $CH_2Cl_2$ (1:9) as eluent. The reaction yielded 53% of 7. Further purification was made by reverse-phase HPLC using a linear gradient of H$_2$O:MeCN (100%->0% H$_2$O) as eluent. $^1$H-NMR (CDCl$_3$) 8.42 (s, 1 H), 8.39 (s, 1 H), 4.64 (d, J=7.47 Hz, 1 H), 4.49 (ddd, J=4.63, 8.95, 12.17 Hz, 1 H), 4.13 (dd, J=7.50, 11.14 Hz, 1 H), 4.04 (d, J=2.63 Hz, 1 H), 3.73-3.90 (m, 4 H), 3.68 (dd, J=4.82, 11.17 Hz, 1 H), 3.36 (t, J=7.15 Hz, 4 H), 2.25 (m, 1 H), 2.00-2.20 (m, 2 H), 1.91 (m, 1 H), 1.62 (m, 4 H), 1.55 (m, 2 H), 0.98 (t, J=7.4, 6 H). HRMS calculated mass ($C_{24}H_{39}N_8O_8^+$): 567.2885, observed mass: 567.2894.

(1R,2S,6S)-2-azido-6-hydroxycyclohexyl acetate (8)

To a solution of 4 (416 mg, 2.09 mmol) and pyridine (506 μL, 6.27 mmol) in $CH_2Cl_2$ (10 mL), Tf$_2$O (421 μL, 2.51 mmol) was dropwise added at −10° C. The mixture was left to react for 10 min when it was diluted ($CH_2Cl_2$), washed (HCl (aq) 5%, NaHCO$_3$(aq) sat, brine), dried (MgSO$_4$), filtered and concentrated. The crude was then dissolved in DMF (20 mL). Bu$_4$NNO$_2$ (1810 mg, 6.27 mmol) was added and the mixture was heated to 50° C. After 1 h the mixture was cooled to room temperature. and concentrated. Purification was made by flash chromatography using EtOAc:n-heptan (1:1) as eluent. The reaction yielded 64% of 8. $^1$H-NMR (CDCl$_3$) 4.79 (dd, J=4.78, 9.75 Hz, 1 H), 4.17 (m, 1 H), 3.83 (ddd, J=4.58, 9.84, 11.29 Hz, 1 H), 2.18 (s, 3 H), 2.00-2.10 (m, 1 H), 1.85-1.95 (m, 1 H), 1.70-1.80 (m, 1 H), 1.50-1.65 (m, 2 H), 1.30-1.45 (m, 1 H)

((1R,2R,3S)-2-acetoxy-3-azidocyclohexyl) 2,4,6-tri-O-acetyl-3-azido-3-deoxy 1-thio-β-D-galactopyranoside (9)

To a solution of 8 (64.5 mg, 324 μmol) and pyridine (78.6 μL, 973 μmol) in CH$_2$Cl$_2$ (1.7 mL), was added dropwise Tf$_2$O (65.4 μL, 389 μmol) at −10° C. The mixture was left to react for 1 h when it was diluted (CH$_2$Cl$_2$), washed (HCl(aq) 5%, NaHCO$_3$(aq) sat, brine), dried (MgSO$_4$), filtered and concentrated. The crude was coevaporated in toluene with methyl 2,4,6-tri-O-acetyl-3-azido-3-deoxy-1-thio-β-D-galactopyranoside (Sörme et al. 2002) (108 mg, 311 μmol) and CH$_2$Cl$_2$ (3.2 mL) was added. The mixture was degassed and Et$_3$N (65.0 μL, 467 μmol) was added. The mixture was left to react for 16 h when it was diluted (CH$_2$Cl$_2$), washed (HCl(aq) 5%, brine), dried (MgSO$_4$), filtered and concentrated. Purification was made by flash chromatography using EtOAc:n-heptan (2:3) as eluent. The reaction yielded 43% of 9. $^1$H-NMR (CDCl$_3$) 5.46 (dd, J=1.10, 3.50 Hz, 1 H), 5.12 (t, J=10.07 Hz, 1 H), 4.82 (dd, J=9.45, 10.54 Hz, 1 H), 4.70 (d, J=9.95 Hz, 1 H), 4.10 (d, J=6.61 Hz, 2 H), 3.89 (t, J=6.10 Hz, 1 H), 3.67 (dd, J=3.33, 9.77 Hz, 1 H), 3.35-3.45 (m, 1 H), 2.77-2.87 (m, 1 H), 2.18 (s, 1 H), 2.15 (s, 3 H), 2.14 (s, 3 H), 2.06 (s, 3 H).

((1R,2R,3S)-2-acetoxy-3-(4-(2-fluorophenyl)-1H-1,2,3-triazol-1-yl)-cyclohexyl) 2,4,6-tri-O-acetyl-3-deoxy-3-(4-(2-fluorophenyl)-1H-1,2,3-triazol-1-yl)-1-thio-β-D-galactopyranoside (10)

Compound 9 (8.80 mg, 16.7 μmol), 1-ethynyl-2-fluorobenzene (5.67 μL, 50.0 μmol), CuI (0.634 mg, 5.00 μmol) and DIPEA (8.55 μL, 50.0 μmol) was dissolved in toluene (1 mL). The mixture was heated to 45° C. and left to react for 22 h when it was diluted (CH$_2$Cl$_2$), washed (HCl(aq) 5%, brine), dried (MgSO$_4$), filtered and concentrated. Purification was made by flash chromatography using EtOAc:n-heptan (3:2) as eluent. The reaction yielded 93% of 10.

In the same way compounds 11-13 were prepared:

((1R,2R,3S)-2-acetoxy-3-(4-(3-fluorophenyl)-1H-1,2,3-triazol-1-yl)-cyclohexyl) 2,4,6-tri-O-acetyl-3-deoxy-3-(4-(3-fluorophenyl)-1H-1,2,3-triazol-1-yl)-1-thio-β-D-galactopyranoside (11)

$^1$H-NMR (CDCl$_3$) 7.86 (s, 1 H), 7.81 (s, 1 H), 7.48-7.63 (m, 4 H), 7.35-7.45 (m, 2 H), 7.70-7.10 (m, 2 H), 5.70 (dd, J=9.74, 10.83 Hz, 1 H), 5.62 (d, J=3.24 Hz, 1 H), 5.26 (t, J=10.38 Hz, 1H), 5.20 (dd, J=3.25, 10.97 Hz, 1 H), 4.92 (d, J=9.58 Hz, 1 H), 4.63-4.73 (m, 1 H), 4.10-4.25 (m, 3 H), 3.05-3.15 (m, 1 H), 2.30-2.50 (m, 2 H), 2.00-2.20 (m, 2 H), 2.09 (s, 3 H), 2.09 (s, 3 H), 1.80-1.90 (m, 1 H), 1.90 (s, 3 H), 1.88 (s, 3 H), 1.60-1.70 (m, 1 H)

((1R,2R,3S)-2-acetoxy-3-(4-(4-fluorophenyl)-1H-1,2,3-triazol-1-yl)-cyclohexyl) 2,4,6-tri-O-acetyl-3-deoxy-3-(4-(4-fluorophenyl)-1H-1,2,3-triazol-1-yl)-1-thio-β-D-galactopyranoside (12)

$^1$H-NMR (CDCl$_3$) 7.70-7.85 (m, 6 H), 7.05-7.15 (m, 4 H), 5.70 (t, J=10.20 Hz, 1 H), 5.62 (d, J=2.36 Hz, 1 H), 5.26 (t, J=10.30 Hz, 1H), 5.20 (dd, J=10.44 Hz, 1 H), 4.92 (d, J=9.46 Hz, 1 H), 4.63-4.73 (m, 1 H), 4.10-4.25 (m, 3 H), 3.05-3.15 (m, 1 H), 2.30-2.50 (m, 2 H), 2.00-2.20 (m, 2 H), 2.09 (s, 3 H), 2.08 (s, 3 H), 1.80-1.90 (m, 1 H), 1.89 (s, 3 H), 1.87 (s, 3 H), 1.60-1.70 (m, 1 H)

((1R,2R,3S)-2-acetoxy-3-(4-(3-thiopheneyl)-1H-1,2,3-triazol-1-yl)-cyclohexyl) 2,4,6-tri-O-acetyl-3-deoxy-3-(4-(3-thienyl)-1H-1,2,3-triazol-1-yl)-1-thio-β-D-galactopyranoside (13)

$^1$H-NMR (CDCl$_3$) 7.74 (s, 1 H), 7.65-7.70 (m, 3 H), 7.42-7.46 (m, 1 H), 7.35-7.42 (m, 3 H), 5.70 (dd, J=9.72, 10.84 Hz, 1 H), 5.61 (d, J=3.20 Hz, 1 H), 5.25 (t, J=10.40 Hz, 1H), 5.19 (dd, J=3.26, 11.06 Hz, 1 H), 4.91 (d, J=9.64 Hz, 1 H), 4.63-4.73 (m, 1 H), 4.10-4.25 (m, 3 H), 3.05-3.15 (m, 1 H), 2.30-2.50 (m, 2 H), 2.00-2.20 (m, 2 H), 2.09 (s, 3 H), 2.08 (s, 3 H), 1.80-1.90 (m, 1 H), 1.89 (s, 3 H), 1.87 (s, 3 H), 1.60-1.70 (m, 1 H)

((1R,2R,3S)-2-hydroxy-3-(4-(2-fluorophenyl)-1H-1,2,3-triazol-1-yl)-cyclohexyl) 3-deoxy-3-(4-(2-fluorophenyl)-1H-1,2,3-triazol-1-yl)-1-thio-β-D-galactopyranoside (15)

Compound 10 (12.0 mg, 15.6 μmol) was dissolved in NaOMe (0.05 M, 1 mL). After 21 h the mixture was neutralized (Duolite C436) and concentrated. Purification was made by reverse-phase HPLC using a linear gradient of H$_2$O: MECN (100%->0% H$_2$O). The reaction yielded 55% of 15. $^1$H-NMR (MeOD) 8.38 (d, J=3.53 Hz, 1 H), 8.35 (d, J=3.55 Hz, 1 H), 8.08-8.18 (m, 2 H), 7.33-7.43 (m, 2 H), 7.18-7.33 (m, 4 H), 4.92 (dd, 1 H), 4.76 (d, J=9.48 Hz, 1 H), 4.47-4.57 (m, 1 H), 4.28 (dd, J=9.51, 10.55 Hz, 1 H), 4.15 (d, J=2.98 Hz, 1 H), 3.83-3.93 (m, 2 H), 3.76 (dd, J=6.87, 11.35 Hz, 1 H), 3.68 (dd, J=5.19, 11.37 Hz, 1 H), 3.07-3.17 (m, 1 H), 2.28-2.38 (m, 1 H), 2.08-2.25 (m, 2 H), 1.90-2.00 (m, 1 H), 1.60-1.77 (m, 2 H).

In the same way compounds 16-18 were prepared:

((1R,2R,3S)-2-hydroxy-3-(4-(3-fluorophenyl)-1H-1,2,3-triazol-1-yl)-cyclohexyl) 3-deoxy-3-(4-(3-fluorophenyl)-1H-1,2,3-triazol-1-yl)-1-thio-β-D-galactopyranoside (16)

$^1$H-NMR (MeOD) 8.50 (s, 1 H), 8.47 (s, 1 H), 7.55-7.70 (m, 4 H), 7.40-7.50 (m, 2 H), 7.03-7.13 (m, 2 H), 4.89 (dd, 1 H), 4.77 (d, 9.48 Hz, 1 H), 4.47-4.57 (m, 1 H), 4.30 (t, J=10.03 Hz, 1 H), 4.14 (d, J=2.87 Hz, 1 H), 3.83-3.93 (m, 2 H), 3.77 (dd, J=6.77, 11.31 Hz, 1 H), 3.69 (dd, J=5.15, 11.24 Hz, 1 H), 3.07-3.17 (m, 1 H), 2.28-2.38 (m, 1 H), 2.08-2.25 (m, 2 H), 1.90-2.00 (m, 1 H), 1.60-1.77 (m, 2 H).

((1R,2R,3S)-2-hydroxy-3-(4-(4-fluorophenyl)-1H-1,2,3-triazol-1-yl)-cyclohexyl) 3-deoxy-3-(4-(4-fluorophenyl)-1H-1,2,3-triazol-1-yl)-1-thio-β-D-galactopyranoside(17)

$^1$H-NMR (MeOD) 8.42 (s, 1 H), 8.38 (s, 1 H), 7.75-7.95 (m, 4 H), 7.10-7.25 (m, 4 H), 4.89 (dd, 1 H), 4.77 (d, J=9.47 Hz, 1 H), 4.47-4.57 (m, 1 H), 4.29 (dd, J=9.77, 10.33 Hz, 1 H), 4.14 (d, J=2.73 Hz, 1 H), 3.83-3.93 (m, 2 H), 3.77 (dd, J=6.81, 11.34 Hz, 1 H), 3.69 (dd, J=5.24, 11.27 Hz, 1 H), 3.07-3.17 (m, 1 H), 2.28-2.38 (m, 1 H), 2.08-2.25 (m, 2 H), 1.90-2.00 (m, 1 H), 1.60-1.77 (m, 2 H).

((1R,2R,3S)-2-hydroxy-3-(4-(3-thiopheneyl)-1H-1,2,3-triazol-1-yl)-cyclohexyl) 3-deoxy-3-(4-(3-thienyl)-1H-1,2,3-triazol-1-yl)-1-thio-β-D-galactopyranoside (18)

$^1$H-NMR (MeOD) 8.44 (s, 1 H), 8.31 (s, 1 H), 7.70-7.83 (m, 2 H), 7.40-7.65 (m, 4 H), 4.85 (dd, 1 H), 4.76 (d, 9.46 Hz,

1 H), 4.47-4.57 (m, 1 H), 4.28 (dd, J=9.53, 10.50 Hz, 1 H), 4.14 (d, J=2.95 Hz, 1 H), 3.83-3.93 (m, 2 H), 3.77 (dd, J=6.79, 11.35 Hz, 1 H), 3.69 (dd, J=5.17, 11.35 Hz, 1 H), 3.07-3.17 (m, 1 H), 2.28-2.38 (m, 1 H), 2.08-2.25 (m, 2 H), 1.90-2.00 (m, 1 H), 1.60-1.77 (m, 2 H).

((1R,2R,3S)-2-hydroxy-3-(4-(propylcarbamoyl)-1H-1,2,3-triazol-1-yl)-cyclohexyl)-3-deoxy-3-(4-(propylcarbamoyl)-1H-1,2,3-triazol-1-yl)-thio-β-D-galactopyranoside(19)

The compound ((1R,2R,3S)-2-acetoxy-3-(4-(methoxycarbonyl)-1H-1,2,3-triazol-1-yl)cyclohexyl)-3-deoxy-3-(4-(methoxycarbonyl)-1H-1,2,3-triazol-1-yl)-thio-β-D-galactopyranoside (2,4,6)-triacetate (14) was prepared following the procedure described above for compound (6). Compound 14 was dissolved in MeOH (2.0 mL) and propylamine (400 µl). After 16 h, the mixture was concentrated and purified by reverse-phase HPLC (linear gradient of $H_2O$:MeCN 100%->0% $H_2O$) to give 19 (68%). $^1$H-NMR (CDCl$_3$) 8.46 (s, 1 H), 8.40 (s, 1 H), 4.73 (d, J=9.5 Hz, 1 H), 4.50 (ddd, J=4.6, 9.0, 12.2 Hz, 1 H), 4.21 (dd, J=9.5, 10.0 Hz, 1 H), 4.09 (br d, J=2.6 Hz, 1 H), 3.63-3.86 (m, 4 H), 3.08 (m, 1 H), 2.30 (m, 1 H), 2.08-2.23 (m, 2 H), 1.95 (m, 1 H), 1.62 (m, 6 H), 1.55 (m, 2 H), 0.98 (t, J=7.5 Hz, 6 H).

((1R,2R,3S)-2-hydroxy-3-(4-chlorobenzamido)-cyclohexyl)-3-deoxy-3-(4-chlorobenzamido)-thio-β-D-galactopyranoside (22)

Compound 9 (135 mg, 0.263 mmol) was dissolved in DCM (500 µl). NaOMe (500 µl, 0.05 M in MeOH) was added and the mixture was stirred over night. The mixture was neutralized (Duolite C436/H$^+$), filtered and concentrated to give ((1R,2R,3S)-2-hydroxy-3-azidocyclohexyl)-3-deoxy-3-azido-thio-β-D-galactopyranoside (20). A portion of the crude compound 20 (5.0 mg, 13.9 µmol) was dissolved in THF (800 µL) and water (800 µL). PMe$_3$ (139 µmol, 139 µL, 1M in THF) was added. After 1 h, the mixture was concentrated to give ((1R,2R,3S)-2-hydroxy-3-aminocyclohexyl)-3-deoxy-3-amino-thio-β-D-galactopyranoside (21). The crude compound 21 was dissolved in DCM (550 µL) and water (550 µL). 4-Chloro benzoylchloride (30.5 µmol, 3.9 µL) and Na$_2$CO$_3$ (14.7 mg, 139 µmol) was added and the mixture was stirred for 1 h. Concentration and flash chromatography (5 g SiO$_2$, EtOAc), and finally reverse-phase HPLC (linear gradient of $H_2O$:MeCN 100%->0% $H_2O$) gave 22 (0.91 mg, 16% from 9). $^1$H-NMR (CDCl$_3$) 7.85 (m, 4 H), 7.48 (m, 4 H), 4.58 (d, J=10.0 Hz, 1 H), 4.13 (dd, J=2.8, 10.0 Hz, 1 H), 4.03 (d, J=3.2 Hz, 1 H), 3.94 (m, 1 H), 3.82 (t, J=10.0 Hz, 1 H), 3.77-3.64 (m, 3 H), 3.42 (t, J=10.0 Hz, 1 H), 2.97 (m, 1 H), 2.23 (m, 1 H), 2.00 (m, 1 H), 1.80 (m, 1 H), 1.60-1.23 (m, 3 H).

Examples of In Vivo Efficacy of Galectin Inhibition in Inflammation and Cancer. Inflammation As mentioned above, many studies suggest a role for galectin-3 in enhancement of the inflammatory response. For example, the addition of galectin-3 to neutrophil leukocytes from an inflammatory site, or primed by exposure to LPS, results in increased generation of toxic oxygen radicals. Lactose can inhibit this response (Karlsson et al., 1998; Almquist et al., 2001). In another study (Sano et al., 2000), galectin-3 was found to be chemotactic to macrophages and monocytes, both in vitro and in vivo. Either lactose or the isolated CRD of galectin-3 (galectin 3C), able to bind the same saccharide receptor as galectin-3 but not cross link it (see below), acted as inhibitors of this response. The substances described in the present invention would be much more effective as inhibitors of the above mentioned responses than lactose because they are much more potent galectin-3 inhibitors. They would also be much more useful in vivo than lactose and the galectin-3C because they are small molecules, more hydrophobic and probably more stable to degradation.

Cancer

As mentioned above, several studies of models of human cancer in mice indicate that enhanced expression of galectin-3 results in faster tumor growth and more metastasis (Bresalier et al., 1998; reviewed by Leffler, 2001 and Takenaka et al in Leffler (editor), 2004b). Injection of a saccharide with inhibitory potency to galectin-3, but perhaps also other proteins, was reported to diminish prostate cancer in rat (Pienta et al., 1995). Hence, potent small-molecule inhibitors of galectin-3 are expected to have similar anticancer effects as galectin-3C (John et al., 2003).

REFERENCES

Almkvist, J., Fäldt, J., Dahlgren, C., Leffler, H., and Karlsson, A. (2001) Lipopolysaccharide-induced gelatinase granule mobilization primes neutrophils for activation by galectin-3 and f-Met-Leu-Phe. *Infect. Immun. Vol.* 69: 832-837.

Barondes, S. H., Cooper, D. N. W., Gitt, M. A., and Leffler, H. (1994). Galectins. Structure and function of a large family of animal lectins. *J. Biol. Chem.* 269:20807-20810.

Blois, S. M., Ilarregui, J. M., Tometten, M., Garcia, M., Orsal, A. S., Cordo-Russo, R., Toscano, M. A., Bianco, G. A., Kobelt, P., Handjiski, B., et al. (2007). A pivotal role for galectin-1 in fetomaternal tolerance. *Nat Med* 13, 1450-1457.

Cumpstey, I., Sundin, A., Leffler, H. and Nilsson, U. J. (2005) C$_2$-Symmetrical thiodigalactoside bis-benzamido derivatives as high-affinity inhibitors of galectin-3: Efficient lectin inhibition through double arginine-arene intereactions. *Angew. Chem. Int. Ed.* 44: 5110-5112.

Cumpstey, I., Salomonsson, E., Sundin, A., Leffler, H. and Nilsson, U. J. (2008) Double affinity amplification of galectin-ligand interactions through arginine-arene interactions: Synthetic, thermodynamic, and computational studies with aromatic diamido-thiodigalactosides. *Chem. Eur. J.* 14: 4233-4245.

Dam, T. K., and Brewer, C. F. (2008). Effects of clustered epitopes in multivalent ligand-receptor interactions. *Biochemistry* 47, 8470-8476.

Delacour, D., Greb, C., Koch, A., Salomonsson, E., Leffler, H., Le Bivic, A., and Jacob, R. (2007). Apical Sorting by Galectin-3-Dependent Glyco-protein Clustering. *Traffic* 8, 379-388.

Delaine, T., Cumpstey, I., Ingrassia, L., Le Mercier, M., Okechukwu, P., Leffler, H., Kiss, R., and Nilsson, U. J. (2008) Galectin-Inhibitory Thiodigalactoside Ester Derivatives Have Anti-Migratory Effects in Cultured Lung and Prostate Cancer Cells. *J. Med. Chem.* 51, 8109-8114.

Fortin, S., Le Mercier, M., Camby, I., Spiegl-Kreinecker, S., Berger, W., Lefranc, F., and Kiss, R. (2008). Galectin-1 Is Implicated in the Protein Kinase C epsilon/Vimentin-Controlled Trafficking of Integrin-beta1 in Glioblastoma Cells. *Brain Pathol*, 1-11.

Garner, O. B., and Baum, L. G. (2008). Galectin-glycan lattices regulate cell-surface glycoprotein organization and signalling. *Biochem Soc Trans* 36, 1472-1477.

Gendronneau, G., Sidhu, S. S., Delacour, D., Dang, T., Calonne, C., Houzelstein, D., Magnaldo, T., and Poirier, F. (2008). Galectin-7 in the control of epidermal homeostasis after injury. *Mol Biol Cell* 19, 5541-5549.

Glinsky, G. V., Price, J. E., Glinsky, V. V., Mossine, V. V., Kiriakova, G., and Metcalf, J. B. (1996). *Cancer Res* 56, 5319-5324.

Houzelstein, D., Goncalves, I. R., Fadden, A. J., Sidhu, S. S., Cooper, D. N., Drickamer, K., Leffler, H., and Poirier, F. (2004) Phylogenetic Analysis of the Vertebrate Galectin Family. *Mol. Biol. Evol.* 21: 1177-1187

Huflejt, M. E. and Leffler, H. (2004) Galectin-4 in normal tissues and cancer. *Glycoconj. J.* 20: 247-255.

John, C. M., Leffler, H., Kahl-Knutsson, B., Svensson, I., and Jarvis, G. A. (2003) Truncated Galectin-3 Inhibits Tumor Growth and Metastasis in Orthotopic Nude Mouse Model of Human Breast *Cancer. Clin. Cancer Res.* 9:2374-2383.

Karlsson, A., Follin, P, Leffler, H., Dahlgren, C. (1998) Galectin-3 activates the NADPH-oxidase in exudated but not peripheral blood neutrophils. *Blood* 91:3430-3438.

MacKinnon, A. C., Farnworth, S. L., Henderson, N. C., Hodkinson, P. S., Kipari, T., Leffler, H., Nilsson, U. J., Haslett, C., Hughes, J., and Sethi, T. (2008). Regulation of alternative macrophage activation by Galectin-3 controls renal fibrosis following ureteric obstruction. *J. Immun.* 180, 2650-2658.

Lau, K. S., and Dennis, J. W. (2008). N-Glycans in cancer progression. *Glycobiology* 18, 750-760.

Lau, K. S., Partridge, E. A., Grigorian, A., Silvescu, C. I., Reinhold, V. N., Demetriou, M., and Dennis, J. W. (2007). Complex N-glycan number and degree of branching cooperate to regulate cell proliferation and differentiation. *Cell* 129, 123-134.

Leffler, H. and Barondes, S. H. (1986) Specificity of binding of three soluble rat lung lectins to substituted and unsubstituted mammalian beta-galactosides. *J. Biol. Chem.* 261: 10119-10126.

Leffler, H. Galectins Structure and Function—A Synopsis in Mammalian Carbohydrate Recognition Systems (Crocker, P. ed.) Springer Verlag, Heidelberg, 2001 pp. 57-83.

Leffler, H., Carlsson, S., Hedlund, M., Qian, Y. and Poirier, F. (2004) Introduction to galectins. *Glycoconj. J.* 19: 433-440.

Leffler, H., editor, (2004b) Special Issue on Galectins. *Glycoconj. J.* 19: 433-638.

Massa, S. M., Cooper, D. N. W., Leffler, H., Barondes, S. H. (1993) L-29, an endogenous lectin, binds to glycoconjugate ligands with positive cooperativity. *Biochemistry* 32; 260-267.

Perone, M. J., Bertera, S., Shufesky, W. J., Divito, S. J., Montecalvo, A., Mathers, A. R., Larregina, A. T., Pang, M., Seth, N., Wucherpfennig, K. W., et al. (2009). Suppression of autoimmune diabetes by soluble galectin-1. *J Immunol* 182, 2641-2653.

Pienta, K. J., Naik, H., Akhtar, A., Yamazaki, K., Reploge, T. S., Lehr, J., Donat, T. L., Tait, L., Hogan, V., and Raz, A. (1995). Inhibition of spontaneous metastasis in a rat prostate cancer model by oral administration of modified citrus pectin. *J Natl Cancer Inst* 87, 348-353.

Sacchettini, J. C., Baum, L. G., and Brewer, C. F. (2001). Multivalent protein-carbohydrate interactions. A new paradigm for supermolecular assembly and signal transduction. *Biochemistry* 40, 3009-3015.

Saegusa, J., Hsu, D. K., Chen, FLY., Yu, L., Fermin, A., Fung, M. A., and Liu, F. T. (2009). Galectin-3 is critical for the development of the allergic inflammatory response in a mouse model of atopic dermatitis. *Am J Pathol* 174, 922-931.

Salameh, B. A., Leffler, H. and Nilsson, U. J. (2005) *Bioorg. Med. Chem. Lett.* 15: 3344-3346.

Seetharaman, J., Kanigsberg, A., Slaaby, R., Leffler, H., Barondes, S. H., Rini, J. M. (1998) X-ray crystal structure of the human galectin-3 carbohydrate recognition domain at 2.1-A resolution. *J. Biol. Chem.* 273:13047-13052.

Sörme, P., Qian, Y., Nyholm, P.-G., Leffler, H., Nilsson, U. J. (2002) Low micromolar inhibitors of galectin-3 based on 3'-derivatization of N-acetyllactosamine. *ChemBioChem* 3:183-189.

Sörme, P., Kahl-Knutsson, B., Wellmar, U., Nilsson, U. J., and Leffler H. (2003a) Fluorescence polarization to study galectin-ligand interactions. *Meth. Enzymol.* 362: 504-512.

Sörme, P., Kahl-Knutsson, B., Wellmar, U., magnusson, B.-G., Leffler H., and Nilsson, U. J. (2003b) Design and synthesis of galectin inhibitors. *Meth. Enzymol.* 363: 157-169.

Sörme, P., Kahl-Knutsson, B., Huflejt, M., Nilsson, U. J., and Leffler H. (2004) Fluorescence polarization as an analytical tool to evaluate galectin-ligand interactions. *Anal. Biochem.* 334: 36-47.

Thijssen, V. L., Poirer, F., Baum, L. G., and Griffioen, A. W. (2007). Galectins in the tumor endothelium: opportunities for combined cancer therapy. *Blood* 110, 2819-2827.

Toscano, M. A., Bianco, G. A., Ilarregui, J. M., Croci, D. O., Correale, J., Hernandez, J. D., Zwirner, N. W., Poirier, F., Riley, E. M., Baum, L. G., et al. (2007). Differential glycosylation of TH1, TH2 and TH-17 effector cells selectively regulates susceptibility to cell death. *Nat Immunol* 8, 825-834.

The invention claimed is:

1. A compound of the general formula (I):

wherein
the configuration of the pyranose ring is D-galacto;
X is selected from the group consisting of O, S, and SO;
Y and Z are independently selected from being CONH or a 1 H- 1,2,3-triazole ring;
R1 and R2 are independently selected from the group consisting of:
  a) an alkyl group of at least 4 carbons, an alkenyl group of at least 4 carbons, an alkynyl group of at least 4 carbons;
  b) a carbamoyl group, a carbamoyi group substituted with an alkyl group, a carbamoyi group substituted with an aikenyl group, a carbamoyl group substituted with an alkynyl group, a carbamoyl group substituted with an aryl group, a carbamoyl group substituted with an substituted alkyl group, and a carbamoyl group substituted with an substituted aryl group;
  c) a phenyl group substituted with at least one carboxy group, a phenyl group substituted with at least one halogen, a phenyl group substituted with at least one alkyl group, a phenyl group substituted with at least one alkoxy group, a phenyl group substituted with at least one trifluoromethyl group, a phenyl group substituted with at least one trifluoromethoxy group, a phenyl group substituted with at least one sulfo group, a phenyl group substituted with at least one hydroxy group, a phenyl group substituted with at least one carbonyl group, and a phenyl group substituted with at least one substituted carbonyl group;

d) a naphthyl group, a naphthyl group substituted with at least one carboxy group, a naphthyl group substituted with at least one halogen, a naphthyl group substituted with at least one alkyl group, a naphthyl group substituted with at least one alkoxy group, a naphthyl group substituted with at least one sulfo group, a naphthyl group substituted with at least one hydroxyl group, a naphthyl group substituted with at least one carbonyl group, and a naphthyl group substituted with at least one substituted carbonyl group;

e) a heteroaryl group comprising 4 to 18 carbon atoms, and at least one heteroatom selected from N, O and S, wherein the heteroaryl group may be substituted with at least one group selected from a carboxy group, a halogen, an alkoxy group, a sulfo group, an arylamino group, a hydroxyl group, a carbonyl group, and a substituted carbonyl group; and f) a thienyl group, a thienyl group substituted with at least one carboxy group, a thienyl group substituted with at least one halogen, a thienyl thienyl group substituted with at least one alkoxy group, a thienyl group substituted with at least one sulfo group, a thienyl group substituted with at least one arylamino group, a thienyl group substituted with at least one hydroxy group, a thienyl group substituted with at least one halogen, a thienyl group substituted with at least one carbonyl group, and a thienyl group substituted with at least one substituted carbonyl group.

2. The compound according to claim 1, wherein Y is CONH.

3. The compound according to claim 2, wherein the CONH group is linked via the N atom to the pyranose ring.

4. The compound according to claim 1, wherein Z is CONH.

5. The compound according to claim 4, wherein the CONH group is linked via the N atom to the cyclohexane.

6. The compound according to claim 1, wherein Y is a 1H-1,2,3-triazole ring.

7. The compound according to claim 6, wherein the 1H-1,2,3-triazole ring is linked via the N1 atom to the pyranose ring.

8. The compound according to claim 7, wherein $R^1$ is linked to the C4 atom of the 1H-1,2,3-triazole ring.

9. The compound according of claim 1, wherein Z is a 1H-1,2,3-triazole ring.

10. The compound according to claim 9, wherein the 1H-1,2,3-triazole ring is linked via the N1 atom to the cyclohexane.

11. The compound according to claim 10, wherein $R^2$ is linked to the C4 atom of the 1H-1,2,3-triazole ring.

12. The compound according to claim 1, wherein $R^1$ and $R^2$ are independently selected from the group consisting of a carbamoyl group, an alkylated carbamoyl group, an alkenylated carbamoyl group, an arylated carbamoyl group, a phenyl group, a substituted phenyl group, a halogenated phenyl group, a fluorinated phenyl group, a chlorinated phenyl group, a brominated phenyl group, an alkylated phenyl group, an alkenylated phenyl group, a trifluoromethylated phenyl group, a methoxylated phenyl group, a trifluoromethoxylated phenyl group, a naphthyl group, a substituted naphthyl group, a heteroaryl group, a substituted heteroaryl group, a thienyl group, and a substituted thienyl group.

13. The compound according to claim 1, wherein $R^1$ is an alkylated carbamoyl group, a fluorinated phenyl group, or a thienyl group.

14. The compound according to claim 1, wherein $R^2$ is an alkylated carbamoyl group, a fluorinated phenyl group, or a thienyl group.

15. The compound according to claim 1, wherein X is O or S.

16. The compound according to claim 1, wherein said compound is selected from the group consisting of:
- ((1R,2R,3S)-2-hydroxy-3-(4-(N-(1-propyl)-carbamoyl)-1H-1,2,3-triazol-1-yl)cyclohexyl)3-deoxy-(3-(4-(N-(1-propyl)-carbamoyl)-1H-1,2,3-triazol-1-yl))-β-D-galactopyranoside,
- ((1R,2R,3S)-2-hydroxy-3-(4-(2-fluorophenyl)-1H-1,2,3-triazol-1-yl)-cyclohexyl)3-deoxy-3-(4-(2-fluorophenyl)-1H-1,2,3-triazol-1-yl)-1-thio-β-D-galactopyranoside,
- ((1R,2R,3S)-2-hydroxy-3-(4-(3-fluorophenyl)-1H-1,2,3-triazol-1-yl)-cyclohexyl)3-deoxy-3-(4-(3-fluorophenyl)-1H-1,2,3-triazol-1-yl)-1-thio-β-D-galactopyranoside,
- ((1R,2R,3S)-2-hydroxy-3-(4-(4-fluorophenyl)-1H-1,2,3-triazol-1-yl)-cyclohexyl)3-deoxy-3-(4-(4-fluorophenyl)-1H-1,2,3-triazol-1-yl)-1-thio-β-D-galactopyranoside,
- (1R,2R,3S)-2-hydroxy-3-(4-(3-thienyl)-1H-1,2,3-triazol-1-yl)-cyclohexyl)3-deoxy-3-(4-(3-thienyl)-1H-1,2,3-triazol-1-yl)-1-thio-β-D-galactopyranoside,
- (1R,2R,3S)-2-hydroxy-3-(4-(N-(1-propyl)-carbamoyl)-1H-1,2,3-triazol-1-yl)-cyclohexyl)3-deoxy-3-(4-(N-(1-propyl)-carbamoyl)-1H-1,2,3-triazol-1-yl)-1-thio-β-D-galactopyranoside, and
- (1R,2R,3S)-2-hydroxy-3-(4-chlorobenzamido)-cyclohexyl)3-deoxy-3-(4-chlorobenzamido)-1-thio-β-D-galactopyranoside.

17. A pharmaceutical composition comprising a compound according to claim 1 as active ingredient together with a pharmaceutically acceptable adjuvant, diluent, excipient or carrier.

18. The pharmaceutical composition according to claim 17, comprising from 1 to 99% by weight of the active ingredient and from 1 to 99% by weight of a pharmaceutically acceptable adjuvant, diluent, excipient or carrier, with the proviso that the combined amount of the active ingredient and of the pharmaceutically acceptable adjuvant, diluent, excipient or carrier do not constitute more than 100% by weight of the pharmaceutical composition.

19. A compound according to claim 1 for use as a medicament.

* * * * *

UNITED STATES PATENT AND TRADEMARK OFFICE
CERTIFICATE OF CORRECTION

PATENT NO. : 8,703,720 B2  Page 1 of 1
APPLICATION NO. : 13/266960
DATED : April 22, 2014
INVENTOR(S) : Hakon Leffler et al.

It is certified that error appears in the above-identified patent and that said Letters Patent is hereby corrected as shown below:

In the Claims

Column 29, Line 46, Claim 8:

After "lined to the" delete "C4atom" and
Insert -- C4 atom --.

Column 29, Line 52, Claim 11:

After "lined to the" delete "C4atom" and
Insert -- C4 atom --.

Signed and Sealed this
Eighth Day of July, 2014

Michelle K. Lee
*Deputy Director of the United States Patent and Trademark Office*